US008680173B2

(12) United States Patent
Wang et al.

(10) Patent No.: US 8,680,173 B2
(45) Date of Patent: *Mar. 25, 2014

(54) SEQUENTIALLY CROSS-LINKED POLYETHYLENE

(71) Applicant: Howmedica Osteonics Corp., Mahwah, NJ (US)

(72) Inventors: Aiguo Wang, Wayne, NJ (US); John H. Dumbleton, Ridgewood, NJ (US); Aaron Essner, Bloomingdale, NJ (US); Shi-Shen Yau, Berkley Heights, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/658,037

(22) Filed: Oct. 23, 2012

(65) Prior Publication Data
US 2013/0046042 A1 Feb. 21, 2013

Related U.S. Application Data

(63) Continuation of application No. 13/223,422, filed on Sep. 1, 2011, now Pat. No. 8,324,291, which is a continuation of application No. 12/757,394, filed on Apr. 9, 2010, now Pat. No. 8,030,370, which is a continuation of application No. 12/315,994, filed on Dec. 9, 2008, now Pat. No. 7,714,036, which is a continuation of application No. 10/957,782, filed on Oct. 4, 2004, now Pat. No. 7,517,919, which is a continuation of application No. 10/454,815, filed on Jun. 4, 2003, now abandoned.

(60) Provisional application No. 60/386,660, filed on Jun. 6, 2002.

(51) Int. Cl.
*A61F 2/02* (2006.01)
*A61F 2/30* (2006.01)
*A61F 2/00* (2006.01)

(52) U.S. Cl.
USPC ........ 523/115; 522/161; 526/352; 623/22.21; 623/23.58

(58) Field of Classification Search
USPC ........ 523/115; 522/161; 526/352; 623/22.21, 623/23.58
See application file for complete search history.

(56) References Cited

U.S. PATENT DOCUMENTS 2,904,480 A  9/1959  Rainer et al.
3,022,543 A  2/1962  Baird, Jr. et al.

(Continued)

FOREIGN PATENT DOCUMENTS

EP  0 177 552 A1  4/1986
EP  0 218 003 A1  4/1987

(Continued)

OTHER PUBLICATIONS

Birkinshaw, Buggy, Daly, O'Neill, "Mechanism of Ageing in Irradiated Polymers" Polymer Degradation and Stability, vol. 22, pp. 285-294, 1988.

(Continued)

*Primary Examiner* — Duc Truong
(74) *Attorney, Agent, or Firm* — Lerner, David, Littenberg, Krumholz & Mentlik, LLP

(57) ABSTRACT

A method of producing an improved polyethylene, especially an ultra-high molecular weight polyethylene utilizes a sequential irradiation and annealing process to form a highly cross-linked polyethylene material. The use of sequential irradiation followed by sequential annealing after each irradiation allows each dose of irradiation in the series of doses to be relatively low while achieving a total dose which is sufficiently high to cross-link the material. The process may either be applied to a preformed material such as a rod or bar or sheet made from polyethylene resin or may be applied to a finished polyethylene part.

17 Claims, 2 Drawing Sheets

(56) References Cited

U.S. PATENT DOCUMENTS

| | | | |
|---|---|---|---|
| 3,057,791 A | 10/1962 | Anderson, Jr. et al. |
| 3,090,770 A | 5/1963 | Gregorian |
| 3,162,623 A | 12/1964 | Cairus et al. |
| 3,297,641 A | 1/1967 | Werber et al. |
| 3,330,748 A | 7/1967 | Lawton |
| 3,352,818 A | 11/1967 | Meyer et al. |
| 3,362,897 A | 1/1968 | Lawton |
| 3,563,869 A | 2/1971 | Rainer et al. |
| 3,616,365 A | 10/1971 | Stastny et al. |
| 3,758,273 A | 9/1973 | Johnston et al. |
| 3,832,827 A | 9/1974 | Lemelson |
| 3,886,056 A | 5/1975 | Kitamaru et al. |
| 4,226,905 A | 10/1980 | Harbourne |
| 4,241,463 A | 12/1980 | Khovaylo |
| 4,586,995 A | 5/1986 | Randall et al. |
| 4,587,163 A | 5/1986 | Zachariades |
| 4,655,769 A | 4/1987 | Zachariades |
| 4,701,288 A | 10/1987 | Cook et al. |
| 4,813,210 A | 3/1989 | Masuda et al. |
| 4,820,466 A | 4/1989 | Zachariades |
| 4,832,965 A | 5/1989 | Helin |
| 4,916,198 A | 4/1990 | Scheve et al. |
| 4,950,151 A | 8/1990 | Zachariades |
| 5,017,627 A | 5/1991 | Bonfield et al. |
| 5,030,402 A | 7/1991 | Zachariades |
| 5,037,928 A | 8/1991 | Li et al. |
| 5,047,446 A | 9/1991 | DeNicola, Jr. |
| 5,096,654 A | 3/1992 | Craggs et al. |
| 5,153,039 A | 10/1992 | Porter et al. |
| 5,160,464 A | 11/1992 | Ward et al. |
| 5,160,677 A | 11/1992 | Gravener et al. |
| 5,200,439 A | 4/1993 | Asanuma |
| 5,292,584 A | 3/1994 | Howard et al. |
| 5,352,732 A | 10/1994 | Howard |
| 5,414,049 A | 5/1995 | Sun et al. |
| 5,428,079 A | 6/1995 | Bastiaansen et al. |
| 5,449,745 A | 9/1995 | Sun et al. |
| 5,466,530 A | 11/1995 | England et al. |
| 5,508,319 A | 4/1996 | DeNicola, Jr. et al. |
| 5,543,471 A | 8/1996 | Sun et al. |
| 5,552,104 A | 9/1996 | DeNicola, Jr. et al. |
| 5,577,368 A | 11/1996 | Hamilton et al. |
| 5,609,643 A | 3/1997 | Colleran et al. |
| 5,650,485 A | 7/1997 | Sun et al. |
| 5,652,281 A | 7/1997 | Galli et al. |
| 5,728,510 A | 3/1998 | White |
| 5,728,748 A | 3/1998 | Sun et al. |
| 5,753,182 A | 5/1998 | Higgins |
| 5,814,423 A | 9/1998 | Maruyama et al. |
| 5,824,411 A | 10/1998 | Shalaby et al. |
| 5,834,113 A | 11/1998 | Shalaby et al. |
| 5,874,123 A | 2/1999 | Park |
| 5,879,400 A | 3/1999 | Merrill et al. |
| 6,017,975 A | 1/2000 | Saum et al. |
| 6,143,232 A | 11/2000 | Rohr |
| 6,165,220 A | 12/2000 | McKellop et al. |
| 6,168,626 B1 | 1/2001 | Hyon et al. |
| 6,174,934 B1 | 1/2001 | Sun et al. |
| 6,184,265 B1 | 2/2001 | Hamilton et al. |
| 6,228,900 B1 | 5/2001 | Shen et al. |
| 6,281,264 B1 | 8/2001 | Salovey et al. |
| 6,372,814 B1 | 4/2002 | Sun et al. |
| 6,432,349 B1 | 8/2002 | Pletcher et al. |
| 6,494,917 B1 | 12/2002 | McKellop et al. |
| 6,503,439 B1 | 1/2003 | Burstein |
| 6,547,828 B2 | 4/2003 | Scott et al. |
| 6,641,617 B1 | 11/2003 | Merrill et al. |
| 6,664,308 B2 | 12/2003 | Sun et al. |
| 6,818,020 B2 | 11/2004 | Sun et al. |
| 7,384,430 B2 | 6/2008 | Greer et al. |
| 7,462,318 B2 | 12/2008 | Schroeder et al. |
| 7,517,919 B2 | 4/2009 | Wang et al. |
| 7,714,036 B2 | 5/2010 | Wang et al. |
| 8,030,370 B2 | 10/2011 | Wang et al. |
| 2002/0013781 A1 | 1/2002 | Petersen |
| 2002/0037944 A1 | 3/2002 | Shen et al. |
| 2002/0107299 A1 | 8/2002 | Sun et al. |
| 2005/0165495 A1 | 7/2005 | Merrill et al. |

FOREIGN PATENT DOCUMENTS

| | | |
|---|---|---|
| EP | 0 373 800 A1 | 6/1990 |
| EP | 0 376 503 A1 | 7/1990 |
| EP | 2 207 436 | 7/1991 |
| EP | 0 729 981 A1 | 9/1996 |
| EP | 1 065 034 A2 | 1/2001 |
| EP | 1 072 275 A1 | 1/2001 |
| GB | 2 060 469 A | 5/1981 |
| GB | 2 156 733 A | 10/1985 |
| GB | 2 157 298 A | 10/1985 |
| GB | 2 180 815 A | 4/1987 |
| GB | 2 225 551 A | 6/1990 |
| JP | 59071830 A | 4/1984 |
| JP | 8-509148 T | 10/1996 |
| JP | 9-122222 A | 5/1997 |
| JP | 2001-164008 A | 6/2001 |
| JP | 2005-514496 T | 5/2005 |
| WO | 90/11060 A1 | 10/1990 |
| WO | 00/62717 A1 | 10/2000 |
| ZA | 896852 | 9/1989 |

OTHER PUBLICATIONS

Birkinshaw, Buggy, Daly, O'Neill, "The Effect of g Radiation on the Physical Structure and Mechanical Properties of Ultrahigh Molecular Weight Polyethylene" Journal of Applied Polymer Science, vol. 38, 1989, pp. 1967-1973.

Black et al., "Application of Headspace Analysis, Solvent Extraction, Thermal Desorption and Gas Chromatography-Mass Spectrometry to the Analysis of Chemical Warfare Samples Containing Sulphur Mustard and Related Compounds" Journal of Chromatography, vol. 637, pp. 71-80, 1993.

Bosboom, Jeroen C., et al., "Large-voume injection in capillary gas chromatography using a programmed-temperature vaporizing injector in the on-column or solvent-vent injection mode," Journal of Chromatography A, 723 (1996) 384-391.

Bourges, Bureau, Dumonceau, Pascat, "Effects of Electron Beam Irradiation on Antioxidants in Commercial Polyolefins: Determination and Quantification of Products Formed" Packaging Technology and Science, vol. 5, pp. 205-209, 1992.

Bourges, Bureau, Pascat, "Effects of Electron Beam Irradiation on Commercial Polypropylene: Kinetic Study of Antioxidant Degradation" Packaging Technology and Science, vol. 5, pp. 197-204, 1992.

Bourges, Bureau, Pascat, "Effects of Electron Beam Irradiation on the Migration of Antioxidants and Their Degradation Products from Commercial Polypropylene into Food Simulating Liquids" Food Additives and Contaminants, vol. 10, No. 4, pp. 443-452, 1993.

Boyd et al., "Synthesis, Characterization, and Potential use of 2-Dodecylcyclobutanone as a Marker for Irradiated Chicken" J. Agric. Food Chem., vol. 39, pp. 789-792, 1991.

Bragdon CR, et al., A New Polyethylene with Undetectable Wear at 12 Million Cycles, 24th Annual Meeting of the Society for Biomaterials, Apr. 22-26, 1998, San Diego, California, U.S.A., p. 2.

Brinston, "Future Growth in the Gamma Sterilizatio of Disposable Medical Products (DMPs)" Radiat. Phys. Chem., vol. 35, Nos. 1-3, pp. 390-392, 1990.

Brinston, "Gaining the Competitive Edge with Gamma Sterilization" Medical Device Technology, Jun. 1991, pp. 28-33.

Brinston, Wilson, "Converting to Gamma-Radiation Sterilization: An Overview for Medical Device Manufacturers" Medical Device Technology, May 1993, pp. 18-22.

Buchalla, R., et al., "Effects of Ionizing Radiation on Plastic Food Packaging Materials: A Review," Journal of Food Protection, vol. 56, No. 11, pp. 991-997 (Nov. 1993).

Buchalla, R., et al., "Effects of Ionizing Radiation on Plastic Food Packaging Materials: A Review," Journal of Food Protection, vol. 56, No. 11, pp. 998-1005 (Nov. 1993).

Buchalla, R., et al., "Radiation Sterilization of Medical Devices, Effects of Ionizing Radiation on Ulta-high Molecular-Weight Polyethylene," Radiat. Phys. Chem., vol. 46, No. 4-6, pp. 579-585, 1995.

(56) References Cited

OTHER PUBLICATIONS

Buchalla, Von R., et al., Die Strahlensterilisation von Medikalprodukten aus Kunstoffen—eine Übersicht, Teil II, Bundesgesundhbl. Jul. 1994, pp. 298-304.
Buchalla, Von R., et al., Die Strahlensterilisation von Medikalprodukten aus Kunstoffen—eine Übersicht, Teil III, Bundesgesundhbl. Aug. 1994, pp. 347-353.
Buchalla, Von. R., et al., Die Strahlensterilisation von Medikalprodukten aus Kunststoffen-eine Übersicht, Teil I, Bundesgesundhbl. Jun. 1994, pp. 261-268.
Bureiko, Ioffe, "Headspace Analysis of Volatile Impurities in Solid Polymers" Zhurnal Analiticheskoi Khimii, vol. 46, No. 3, pp. 452-460, 1991.
C. Birkinshaw, et al., Plasticization of nylon 66 by water and alcohol, Polymer Communications, 1987, vol. 28, October, pp. 286-288.
C. Birkinshaw, et al., The Effect of Sterilising Radiation on the Properties of Nylon 66, Materials Chemistry and Physics, 17 (1987) pp. 239-248.
C. Sawatari, et al., "Temperature-dependence of mechanical and morphological properties of ultra-high molecular weight polyethylene cross-linked by electron beam irradiation", Colloid & Polymer Science, vol. 226, No. 4 (1988), pp. 316-323.
C.J. Grobbelaar, et al., "The Radiation Improvement of Polyethylene Prostheses", The Journal of Bone and Joint Surgery, vol. 60-B, No. 3, Aug. 1978, pp. 370-374.
C.T. Lue, E.J. Ellis, and A. Crugnola, Effects of Gamma-Irradiation on Ultra-High-Molecular-Weight Polyethylene, Proceedings of the Annual Meeting of the Society of Plastics Engineers, vol. 39, pp. 246-247 (1981).
C.T. Lue, et al., "Approaching the Properties of UHMW-PE by Crosslinking Low Molecular Weight HDPE", ANTEC '84, pp. 538-541.
Camino, Giovanni, "Hyphenated Techniques in Polymer Characterization: Thermal-Spectroscopic and Other Methods (ACS Symposium Series No. 581"), p. 246, Jul. 1996.
Cates, Faris, Keating, Ritter, "Polyethylene Wear in Cemented Metal-Backed Acetabular Cups", The Journal of Bones and Joint Surgery, Vo. 75-B, No. 2, Mar. 1993, pp. 249-253.
Chapiro, A., "Physical and Chemical Effects of Ionizing Radiations on Polymeric Systems" in "Technical Developments and Prospects of Sterilization by Ionizing Radiatio," International Conference, Vienna, Austria, Apr. 1-4, 1974.
Charlesby, "Past and Future Trends in Polymer Irradiation" Radiat. Phys. Chem., vol. 37, No. 1, pp. 5-10, 1991.
Chin, "Gamma Sterilization and Single-Use Devices" pp. 21-23.
Ching-Tai Lue, Effects of Gamma Irradiation and Post Heat-Treatments on the Structure and Mechanical Properties of Ultra High Molecular Weight Polyethylene (UHMW-PE), Jun. 15, 1979.
Chris Saunders et al., "Radiation Effects on Microorganisms and Polymers for Medical Products", Radiation Effects on Polymers, pp. 89-92, 1991.
Chuaqui-Offermanns, "Food Packaging Materials and Radiation Processing of Food: A Brief Review" Radiat. Phys. Chem., vol. 34, No. 6, pp. 1005-1007, 1989.
Chuaqui-Offermanns, "Recent Advances in the Identification of Irradiated Foods of Animal Origin: A Review" J. of Radiation Sterilization, vol. 1, pp. 29-41, 1992.
Code of Federal Regulations, Food and Drugs 21, Parts 170 to 199, Revised as of Apr. 1, 1989.
Collier, Sperling, Currier, Sutula, Saum and Mayor, "Impact of Gamma Sterilization on Clinical Performance of Polyethylene in the Knee", Journal of Arthroplasty, vol. 11, No. 4, 1996, pp. 377-388.
Combined Chemical and Mechanical Effects on Free Radicals in UHMWPE Joints During Implantation, Jnl. Biomed Mater. Research, vol. 25, 1991.
Cook, Mratogla, Jasty, Harris, "The Effect of Molecular Weight on the Cross-Link Density of Irradiated Ultra-High Molecular Weight Polyethelenes", 24th Annual Meeting of the Society for Biomaterials, Apr. 1998. p. 153.

Costa, Luda, Trossarelli, del Prever, Croval and Gallinaro, "In vivo UHMWPE biodegradation of retrieved prosthesis" Boimaterials 19 (1998), 1371-1385.
D.A. Baker, et a., Study of fatigue resistance of chemical and radiation crosslinked medical grade ultrahigh molecular weight polyethylene, Mar. 26, 1999, pp. 573-581.
D.A. Blackadder et al., "Annealing of high density polyethylene for very long times at low supercooling under vacuum", Polymer, 1972, vol. 13, December, pp. 584-586.
D.A. Blackadder, et al., "Properties of polymer crystal aggregates. (2) Annealing of polyethylene crystal aggregates", pp. 147-164, 1969.
D.C. Waterman et al., "The Radiation Chemistry of Polyethylene. X. Kinetics of the Conversion of Alkyl to Allyl Free Radicals", The Radiation Chemistry of Polyethylene, vol. 74, No. 9, Apr. 30, 1970, pp. 1913-1922.
D.F. Gibbons, et al, Wear and Degradation of Retrieved Ultrahigh Molecular Weight Polyethylene and Other Polymeric Implants, American Soceity for Testing and Materials, 1979, pp. 20-40.
D.J. Carlsson et al, "Polypropylene Degradation by ?-Irradiation in Air", Polymer Stabilization and Degradation, pp. 359-371, 1985.
D.J. Dijkstra et al., Cross-linking of ultra-high molecular weight polyethylene in the melt by means of electron beam irradiation, Polymer, 1989, vol. 30, May, pp. 866-770.
D.J. Dijkstra, et al. "Cross-linking of porous gel-spun ultra-high molecular weight polyethylene by means of electron beam irradiation", Polymer Bulletin, vol. 20, pp. 557-582, (1988).
D.J. Dijkstra, et al. "Cross-linking of porous gel-spun ultra-high strength polyethylene fibers by means of electron beam irradiation", Polymer Bulletin, vol. 17, pp. 507-513, (1987).
D.J. Dijkstra, W. Hoogsteen, and A.J. Pennings, "Cross-Linking of Ultra-High Molecular Weight Polyethylene in the Melt by Means of Electron Beam Irradiation," Polymer, vol. 30, pp. 866-873 (May 1989).
D.T. Turner, "The Influence of the Temperature of Irradiation on the Formation of Polymer Networks", Polymer Letters, vol. 1, pp. 101-103 (1963).
Wright and Bartel, "The Problem of Surface Damage in Polyethylene Total Knee Components", Clinical Orthopaedics and Related Research, No. 205, Apr. 1986.
Wright, Burstein and Bartel, "Retrieval Analysis of Total Joint Replacement Components: A Six-Year Experience", Corrosion and Degradation of Implant Materials, pp. 414-428.
Wroblewski, "Wear of High-Density Polyethylene on Bone and Cartilage" The Journal of Bone and Joint Surgery, pp. 498-500.
Wroblewski, B.M., et al., "Prospective Clinical and Joint Simulator Studies of a New Total Hip Arthroplasty Using Alumina Ceramic Heads and Cross-Linked Polyethylene Cups," The Journal of Bone and Joint Surgery, vol. 78-B, No. 2, Mar. 1996, pp. 280-285.
Wrona, Mayor, Collier and Jensen, "The Correlation Between Fusion Defects and Damage in Tibial Polyethylene Bearings", Clinical Orthopaedics and Related Research, No. 299, pp. 92-103, 1994.
Yeh and Runt, "Fatigue Crack Propagation in High-Density Polyethylene", Journal of Polymer Science, vol. 29, pp. 371-388 (1991).
Yoshihiro Sakai, et al., Effect of electron beam irradiation on simultaneously biaxially drawn ultra-high molecular weight polyethylene dried gel films, POLYMER, 1993, vol. 34, No. 16, pp. 3362-3345.
Yoshii, Makuuchi, Ishigaki, "Durability of Radiation-Sterilized Polymers: Radiation Resistance of High Molecular Weight Polypropylene" Polymer Communications, 1987, vol. 28, October, pp. 278-280.
Young Lie Chen et al., "Photocrosslinking of Polyethylene. I. Photoinitiators, Crosslinking Agent, and Reaction Kinetics", Journal of Polymer Science, Part A. Polymer Chemistry, vol. 27, No. 12, Nov. 1989, pp. 4051-4075.
Yousefi, A. and et al., "Post Irradiation Degradation of Polypropylene Radiation Durability of Polypropylene Stabilized with Phenolic Stabilizers(II)," Radiat. Phys. Chem., vol. 44, No. 6, ppl. 645-649, 1994.
Zachariades, Logan, "The Melt Anisotropy of Ultrahigh-Molecular-Weight Polyethylene" Journal of Polymer Science, vol. 21, pp. 821-830.
D.T. Turner, The Influence of the Temperatures of Irradiation on the Formation of Polymer Networks, vol. 1, pp. 101-103 (1963).

(56) References Cited

OTHER PUBLICATIONS

D.W. Clegg and A.A. Collyer (Eds.), Irradiation Effects on Polymers (Elsevier Applied Science 1991).
Daniel O. O'Connor, et al., Wear and High Cycle Fatigue of a Highly Crosslinked UHMWPE, 1999 Society for Biomaterials, 25th Annual Meeting Transactions, pp. 508, 520 and 463.
David H. Sochart, MB, ChB, MD, Relationship of Acetabular Wear to Osteolysis and Loosening in Total Hip Arthroplasty, Clinical Orthopaedics and Related Research, No. 363, pp. 135-150.
David N. Collins, et al., Fractury of the Acetabular Cup, The Journal of Bone and Joint Surgery, vol. 64-A, No. 6, Jul. 1982, pp. 939-940.
De Gante, C. Rojas and Pascart, "Effects of B-ionizing Radiation on the Propert9ies of Flexible Packaging Materials", Packaging Technology and Science vol. 3 97-115 (1990).
Delincé, Henry, "Detection of food treated with ionizing radiation," Trends in Food Science & Technology 9 (1998) 73-82.
Demertzis, Panagiotis G., et al., "The Effects of g-Irradiation on Compositional Changes in Plastic Packaging Films," Packag. Techinol. Sci. 12, 119-130 (1999).
Dempsey, Thirucote, "Sterilization of Medical Devices: A Review" Journal of Biomaterials Applications, vol. 3, Jan. 1989, pp. 454-523.
Department of Health, Education, and Welfare, Ethylene Oxide, Ethylene Chlorohydrin, and Ethylene Glycol, Federal Register, vol. 43, No. 122—Friday, Jun. 23, 1978, pp. 27474-24783.
Derbyshire, "The LomoR Process: A Solution for Residual Monomers?" Radiat. Phys. Chem., vol. 14, pp. 333-342, 1979.
Derbyshire, Fisher, Dowson, Hardaker and Brummitt, "Comparative sudy of the wear of UHMWPE with zirocnia ceramic and stainless steel femoral heads in aftrtifical hip joints", Med. Eng. Phys, 1994, vol. 16, 229-236, May.
Deschenes et al., "Irradiation of a Barrier Film: Analysis of Some Mass Transfer Aspects" Radiat. Phys. Chem., vol. 46, No. 4-6, pp. 805-808, 1995.
Devane, Bourne, Rorabeck, MacDonald and Robinson, "Measurement of Polyethylene Wear in Metal-Backed Acetabular Cups", Clinical Orthopaedics and Related Research, No. 319, pp. 317-326, 1995.
Devane, Horne, Martin, Coldham and Krause, "Three-dimensional Polyethylene Wear of a Press-fit Titanium Prosthesis: Factors Influencing Generation of Polyethylene Debris", Journal of Arthroplasty, vol. 12, No. 3, 1997, pp. 256-265.
Devane, Robinson, Bourne, Rorabeck, Nayak and Horne, "Measurement of Polyethelene Wear in Acetabular Components Inserted with and without Cement", Journal of Bone and Joint Surgery, vol. 79-A, No. 5, May 1997.
Dimaio, Saum, Lilly, Moore, "Effect of Radiation Dose on the Physical Properties of Crosslinked UHMWPE", 45th Annual Meeting, Orthopedic Research Society, Feb. 1999.
Dorpema, "Review and State of the Art on Radiation Sterilization of Medical Devices" Radiat. Phys. Chem., vol. 35, No. 1-3, pp. 357-360, 1990.
Dumbleton et al., "The Basis for a Second-generation Highly Crosslinked UHMWPE", Clinical Orthopaedics and Related Research, No. 453, pp. 265-271, 2006.
E. Ergoz, et al., Molecular Weight Dependence of the Crystallization Kinetics of Linear Polyethyelen. I. Experimental Results, Crystallization Kinetics of Linear Polyethylene, vol. 5, No. 2, Mar.-Apr. 1972, pp. 147-157.
Edidin et al. "Plasticity-Induced Damage Layer Is a Precursor to Wear in Radiation-Cross-Linked UHMWPE Acetabular Components for Total Hip Replacement", The Journal of Arthroplasty, vol. 14, No. 5, 1999.
Edidin, Pruitt, Jewett, Crane, Roberts and Kurtz, "Plasticity-Induced Damage Layer Is a Precursor to Wear in Radiation-Cross-Linked UHMWPE Acetabular Components for Total Hip Replacement", Journal of Arthroplasty, vol. 14, No. 5, 199, pp. 616-627.
Edward S. Grood, Ph.D. And Frank R. Noyes, M.D., Cruciate Ligament Prosthesis: Strength, Creep, and Fatigue Properties, From the Orthopaedic Biomechanics Laboratory, Department of Orthopaedic Surgery, University of Cincinnati Medical Center, Cincinnati, vol. 58-A, No. 8, Dec. 1976.
Ellis, "Medical Markets for Radiation Sterilizable Plastics" pp. 31-34.
Eyerer, Ke, "Property Changes of UHMW Polyethylene Hip Cup Endoprostheses During Implantation" Journal of Biomedical Materials Research, 1984, vol. 18, pp. 1137-1151.
F. Wele, R. Franz, "Frage nach Qualitatsverlust berechtigt? EinfluB ionisierender Strahlen auf Verpackungen and Auswirkungen auf die Lebensmittel", ZFL 50 (1999) No. 4.
F.C. Ewald, M.D., et al. Duo-Patella Total Knee Arthroplasty in Rheumatoid Arthritis, American Academy of Orthopaedic Surgeons, p. 202.
Feazel, Burks, Moses, Tripp, "Testing Packages for Irradiated Foods" Package Engineering, vol. 5, No. 4, pp. 43-45, 1960.
Ferdinand Rodriguez, Principles of Polymer Systems, Second Edition, pp. 216-218, 1982.
Fisher, Eng, Hailey, Shaw and Stone, "Preliminary Study of the Effect of Aging Following Irradiation on the Wear of Ultrahigh-molecular-weight Polyethylene", Journal of Artroplasty, vol. 10, No. 5, 1995.
Foden and Morrow, "Influence of Molecular Weight on Fatigue Behavior of Polyethylene and Polystyrene", Polymer Engineering and Science, Apr. 1977, vol. 17, No. 4.
Francis Cracco, et al., "ESR Studied of Free Radical Decay in Irradiated Polyethylene", The Journal of Chemical Physics, vol. 37, No. 10, Nov. 15, 1962, pp. 2449-2457.
Francis Cracco, et al., ESR Studies of Free Radical Decay in Irradiated Polyethylene, The Journal of Chemical Physics, vol. 37, No. 10, Nov. 15, 1962, pp. 2449-2457.
Francis Francis, et al., The Velocity of Oxidation of Paraffin Wax, Parts I-IV, Dec. 20, 1923, pp. 381-393.
Francis Francois, et al., The Non-Acidic Oxidation Products of Paraffin Wax, Received, May 22nd, 1926, pp. 2377-2834.
Fred W. Billmeyer, Jr., Textbook of Polymer Science, 3rd Edition, pp. 312-314, 1984.
Frohnsdorff, "Sterilisation of Medical Products in Europe" Radiat. Phys. Chem. vol. 17, pp. 95-106, 1981.
Fujita, "Organic Vapors Above the Glass Transition Temperature" Diffusion in Polymers, pp. 75-105.
G. A. Schreiber et al, "Detection of irradiated food—methods and routine applications" Int. J. Riadia. Biol., 1993, vol. 63, No. 1, 105-130.
G. Akay, F. Cimen, and T. Tincer, The Effects of Molecular Orientation on Gamma-Radiation Induced Crosslinking in High Density Polyethylene, Radiation Physics and Chemistry, vo. 36, pp. 337-343 (1990).
G. Gielenz and B.J. Jungnickel, Crystalline and Supermolecular Structures in Linear Polyethylene Irradiated With Fast Electrons, Colloid and Polymer Science, vol. 260, pp. 742-753 (1982).
G. Schulzki, "Detection of Radiation-Induced Hydrocarbons in Baked Sponge Cake Prepared with Irradiated Liquid Egg", Radia. Phys. Chem. vol. 46, No. 4-6, pp. 765-769, 1995.
G.E.Tripp, "Packaging for Irradiated Foods", Intl. Journal of Applied Radiation and Isotopes, 1959, vol. 6 pp. 199-206.
G.W. Halldin and S.D. Mehta, The Effect of Particle Characterics on the Sintering Behavior of Ultra-High Molecular Weight Polyethylene, Department of Mechanical Engineering, University of Wisconsin-Madison, Madison, Wisconsin, 53706, pp. 238-241.
Gene M. Farling and Keith Greer, An Improved Bearing Material for Joint Replacement Prostheses: Carbon Fibre-reinforced Ultra High Molecular Weight Polyethylene, Mechanical Properties of Biomaterials, Chapter 4, 1980, pp. 53-64.
Gilbert, Shepherd, "Headspace Gas Chromatography for the Analysis of Vinyl Chloride and Other Monomers in Plastic Packaging and in Foods" Journal of the Association of Public Analysts, Vol. 19, pp. 39-49, 1981.
Gilbert, Startin, "A Survey of Styrene Monomer Levels in Foods and Plastic Packaging by Coupled Mass Spectrometry—Automatic Headspace Gas Chromatography" J. Sci. Food Agric., vol. 34, pp. 647-652, 1983.

(56) References Cited

OTHER PUBLICATIONS

Gilburt, Ingram, Scott, Underhill, "The Analysis of Clingfilms by Infrared Spectroscopy and Thermal Desorption Capillary Gas Chromatography" JFSS, vol. 31, pp. 337-347, 1991.

Gillis, Schmieg, Bhattacharyya and Li, An Independent Evaluation of the Mechanical Chemical and Fracture Properties of UHMWPE Cross Linked by 34 Different Conditions, 45th Annual Meeting, Orthopaedic Research Society, Feb. 1999.

Gladius Lewis, Design Issues in Clinical Studies of the in Vivo Volumetric Wear Rate of Polyethylene Bearing Components, The Journal of Bone and Joint Surgery, Incorporated, vol. 82-A, No. 2, Feb. 2000, pp. 281-296.

Hood, Wright, Burstein, Insall, "Retrieval Analysis of Fifty-Seven Total Condylar Knee Prostheses" 27th Annual ORS, Feb. 24-26, 198, p. 159.

Hopson et al., "Geometric Total Knee Replacement: An Eight Year Experience at the New England Baptist Hospital" Orthopedics, Jun. 1980, vol. 3, No. 6, pp. 537-546.

Hornbogen, "Mikrostruktur und Verchleib" pp. 79-103.

Horng, Klemchuk, "Stabilizers in Gamma-Irradiated Polypropylene" Plastics Engineering, Apr. 1984, pp. 35-37.

Housel, "Additives Help Hold Color in Gamma-Sterilized PVC" Plastics Engineering Sep. 1985, pp. 47-49.

Hsu, Walker, "Wear and Deformation of Patellar Components in Total Knee Arthroplasty" Orthopedic Biomechanics Laboratory, Brigham and Women's Hospital, Boston, Patellar Components in TKA, pp. 260-265.

Hugh U. Cameron, M.D., et al. The Patella in Total Knee Arthroplasty, Clinical Orthopaedics and Related Research, No. 165, May 1982, pp. 197-199.

Hugh U. Cameron, MB, ChB, et al., The Patellar Meniscus in Total Knee Replacement, Orthopaedic Review, vol. XVI, No. 3, Mar. 1987, pp. 75-77.

I.C. Clarke, et al., Fluid-sorption phenomena in sterilized polyethylene acetabular prostheses, Biomaterials, 1985, vol. 6, May, pp. 184-188.

I.C. Clarke, Ph.D., et al., Can Wear in Total Hip Arthroplastics Be Assessed from Radiographs?, Clinical Orthopaedics and Releated Research, No. 121, Nov.-Dec. 1976, pp. 126-142.

Install, J, Binazzi, R., "Total Knee Arthroplasty", Clinical Orthopedics and Related Research, pp. 13-22, No. 192, Jan. 1985.

Iring, M., Kelen T., Fodor, Z., Tudos, F., "Thermo-Oxidative Degradation of Polyolefines, 11. Comparison of Polyethylene Oxidation in Solution and in Meit", Polymer Bulletin:7:489-495, 1982.

Isidore Cohn, Jr., et al., Infections, Principles of Surgery/Basic Considerations, Chapter 5, pp. 181-215.

J. Charnely, et al., The Optimum Size of Prosthetic Heads in Relation to the Wear of Plastic Sockets in Total Replacement of the Hip, Med. & Biol. Engng. vol. 7, pp. 31-39, Pergamon Press, 1969, pp. 31-39.

J. de Boer et al., "Crosslinking of ultra-high molecular weight polyethylene in the oriented state with dicumylperoxide", Polymer, 1984, vol. 25, April, pp. 513-519.

J. H. Dumbleton, et al., A Study of the Wear of Some Materials in Connection With Total Hip Replacement, Wear, 29 (1974), pp. 163-171.

J.H. Dumbleton and C. Shen, The Friction and Wear of Very High Molecular Weight Polyethylene, Journal of Applied Polymer Science, vol. 18 (1974), pp. 3493-3496.

J.H. Dumbleton and C. Shen, The Wear Behavior of Ultrahigh Molecular Weight Polyethyelene, Wear, 37 (1976), pp. 279-289.

J.R. Atkinson, et al., The Wear of High Molecular Weight Polyethylene Part 1: The Wear of Isotropic Polyethyelen Against Dry Stainless Steel in Unidirectional Motion, Journal of Lubrication Technology, Apr. 1978, vol. 100, pp. 208-218.

Jackson, Windler and Simon, "Intraarticular Reaction Associated with the use of Freeze-dried, Ethylene Oxide-sterilized bone-patella Tendon-bone Allografts in the Reconstruction of the Anterior Curciate Ligament", The American Journal of Sports Medicine, vol. 18, No. 1, 1990, pp. 1-11.

Jacobs, Black, Composite Implants for Orthopedic Applications: In Vivo Evaluation of Candidate Resins, J. Biomed. Matter Res. Symposium, No. 6, pp. 221-225 (1975).

Jacobsson, "Analysis of Volatile Organic Compounds in Polymers by Dynamic Headspace and Gas Chromatography/Mass Spectrometry" Journal of High Resolution Chromatography, vol. 7, pp. 185-190, Apr. 1984.

Jaeger, "Moving Sources of Heat and the Temperature at Sliding Contacts" 1942, pp. 203-224.

James C. Bayley, M.D. et al., Failure of the Metal-Backed Patellar Component After Total Knee Repacement, The Journal of Bone and Joint Surgery, vol. 70-A, No. 5, Jun. 1988, pp. 668-674.

James, Lee, Beauregard, Rentfrow and McLaughlin, "Clinical Wear of 63 Ultrahigh Molecular Weight Polyethylene Acetabular Components: Effect of Starting Resin and Forming Method", Biomed Matter Res 48:374-384, 1999.

Jasty, Goetz, Bragdon, Hanson, Elder and Harris, "Wear of Polyethylene Acetabular Components in Total Hip Arthroplasty", Journal of Bone and Joint Surgery, vol. 79-A, No. 3, Mar. 1997.

Jeffrey R. Ellis, PhD, Packaging/Sterilization EtO: Does It Have a Future?, Circle Reader Service #62, Feb. 1990, pp. 50-51.

John Charnley, C.B.E., F.R.S. and David K. Halley, M.D., Rate of Wear in Total Hip Replacement, Clinical Orthopaedics and Releated Research, No. 112, Oct. 1975, pp. 170-179.

John Charnley, D.S.c., F.R.C.S. And Zoran Cupic, M.D., The Nine and Ten Year Results of the Low-Friction Arthroplasty of the Hip, Clinical Orthopaedics and Related Research, No. 95, Sep. 1973, pp. 9-25.

John Charnley, The Long-Term Results of Low-Friction Arthroplasty of the Hip Performed as a Primary Intervention, The Journal of Bone and Joint Surgery, vol. 54B, No. 1, Feb. 1972, pp. 61-76.

John J. Callaghan, MD., et al., Radiographic Measurement of Wear in 5 Cohorts of Patients Observed for 5 to 22 Years, Clinical Orthopaedics and Related Research, No. 317, pp. 14-18.

John N. Insall, M.D., et al., The Posterior Stabilized Condylar Prosthesis: A Modification of the Total Condylar Design, From the Hospital for Special Surgery, Affiliated with the New York Hospital-Cornell University of Medical College, New York City, vol. 64-A, No. 9, Dec. 1982.

Jonathan Black, Ph.D., Orthopaedic Biomaterials in Research and Practice, pp. 144-150, 1988.

Jorge O. Galanta and William Rostoker, Wear in Total Hip Prosthesis, Acta Orthopaedica Scandinavica, Supplementum No. 145, 1973, pp. 1-46.

Jorge O. Galante and William Rostoker, Wear Rates of Candidate Materials for Total Hip Arthroplasty, Proceedings of the first open scientific meeting of The Hip Society, 1973, pp. 65-78.

Judith M. Dowling, et al., The Characteristics of Acetabular Cups Worn in the Human Body, The Journal of Bone and Joint Surgery, vol. 60-B, No. 3, Aug. 1978, pp. 375-382.

Junkichi Sohma, "Radical Migration as an Elementary Process in Degradation", vol. 55, No. 10, pp. 1595-1601, 1983.

K. Grob, G. Grob, Grob, Jr., "Testing Capillary Gas Chromatographic Columns" Journal of Chromatography, vol. 219, pp. 13-20, 1981.

K.E. Elbert, et al., Fatigue Crack Propagation Behavior of Ultra High Molecular Weight Polyethylene Under Mixed Mode Conditions, Journal of Biomedical Materials Research, vol. 28, 181-187 (1994), pp. 181-187.

K.J. Brown, et al., The Wear of Ultrahigh Molecular Weight Polyethylene and a Preliminary Study of Its Relation to The In Vivo Behaviour of Replacement Hip Joints, Wear, 40 (1976), pp. 255-264.

Kabo, Gebhard, Loren, Amstutz, "In Vivo Wear of Polyethylene Acetabular Components", The Journal of Bone and Joint Surgery, vol. 75-B, No. 2, Mar. 1993, pp. 254-258.

Kaltwasser, Uenatusu, Walker, "The Patello-Femoral Joint in Total Knee Replacement", 33 rd Annual Meeting, Orthopaedic Research Society, Jan. 19-22, 1987, San Francisco.

Karkkainen, Seppala, Himberg, "Detection of Trace Levels of Gasoline in Arson Cases by Gas Chromatography-Mass Spectrometry with an Automatic On-line Thermal Desorber" Journal of Forensic Sciences, pp. 186-193.

(56) References Cited

OTHER PUBLICATIONS

Keay, "The Effect of Doses of Gamma Radiation up to 16 Mrad on Plastic Packaging Materials for Fish" J. Fd. Technol., vol. 3, pp. 123-129, 1968.

Kenneth R. St. John, et al., Comparison of the Wear Resistance of Two Cross-Linked Polyethylene Materials, 1999 Society for Biomaterials, 25th Annual Meeting Transactions, pp. 501 and 783.

Kilcast, "Irradiation of Packaged Food" Food Irradiation and the Chemist, pp. 140-152.

Killoran, John J., "Chemical and Physical Changes in Food Packaging Materials Exposed to Ionizing Radiation," Radiation Res. Rev., 3 (1972) 369-388.

Kim J. Chillag, M.D., et al., An Analysis of Polyethylene Thickness in Modular Total Knee Components, Clinical Orthopaedics and Related Research, No. 273, Dec. 1991, pp. 261-263.

Kim-Kang et al., "Isolation and Identification of Potential Migrants in Gamma-Irradiated Plastic Laminates by using GC/MS and GC/IR," Applied Spectroscopy, vol. 45, No. 4 (1991), pp. 572-580.

Kim-Kang et al., "Permeation Characteristics of and Extractables from Gamma-irradiated and Non-irradiated Plastic Laminates for a Unit Dosage Injection Device," Packaging Technology and Science, vol. 4, 35-48 (1991).

P. Eyerer, Material Analysis of Retrieved UHMW Polyethylene (UHMW PE), Biomed Technik, 28 (1983), pp. 297-309.

P. Griss, et al., Findings on Total Hip Replacement for Ten Years, National Library of Medicine, Feb. 8, 1982, pp. 1-22.

P. Wunsche, Generation of Free Radicals by Increasing the Temperature after g-Irradiation of Polyethylene, Journal of Macromolecular Science-Physics, v. B23, pp. 65-84 (1984).

P.J. Tayler et al, "Thermal Description—Gas Chromatography—Mass Spectrometry Studies of commercial polypropylene samples", International Journal of Mass Spectrometry and Ion Processes, 89 (1989) 157-169.

Pargas, Threshold of Regulation is 'sensible' option for meat irradiaton packaging, FDA's Hansen tesll AMI seminar, Foof Chemical News, Feb. 23, 1998, pp. 9-11.

Pascaud, Evans, McCullagh and FitzPatrick, "Effects of batch to batch variations and test methodology on degree of crystallinity and melting temperature of UHMW-PE as measured by differential scanning calorimetry", Journal of Biomedical Materials Research, vol. 32, 619-626 (1996).

Patel, et al., "Crystallinity and the Effect of Ionizing Radiation in Polyethylene. I. Crosslinking and Crystal Core; II. Crosslinking in Chain-Folded Single Crystals; III. An Experiment on the Irradiation-Inducted Crosslinking in n-Hexatriacontane", Journal of Polymer Science: Polymer Physics Edition, vol. 13, pp. 303-338, (1975).

Patel, Keller, "On the Effect of Ionizing Radiation on Hydrocarbons and Polyethylene in Their Crystalline State" Polymer Letters Edition, vol. 11, pp. 737-743, 1973.

Paul Ducheyne, Ph.D., et al., Failure of Total Knee Arthroplasty Due to Loosening and Deformation of the Tibial Component, The Journal of Bone and Joint Surgery, vol. 60-A, No. 3, Apr. 1978, pp. 384-391.

Pearson, "The 1993 Medical Device Technology Raw Materials Survey", Medical Device Technlology, pp. 38-41 September.

Pearson, Lynn Sash "The 1993 Medical Device Technology Sterilization Survey", pp. 42-44, 46, Medical Device Technology May 1993.

Pizzoferrato, "Evaluation of the Tissue Response to the Wear Products of the Hip Joint Endo-Arthroprosthesis" Biomat., Med. Dev., Art. Org., vol. 7, pp. 257-262, 1979.

Plester, D.W., "The sterilization of plastics" Trans J. Plastics Inst., pp. 579-585, Aug. 1967.

Pokrop, "Sterilization: Humidification of Preconditioning Rooms in EtO Sterilization", Technology, Jan. 1992.

Polypropylene Degradation by 2-Irradiation in Air, American Chemical Society, 1985, pp. 359-371.

Pooley, Tabor, "Friction and Molecular Structure: The Behaviour of Some Thermoplastics" Proc. R. Soc. Lond. A, vol. 329, pp. 251-274, 1972.

Premnath, V., et al., Melt Irradiated UHMWPE for Total Hip Replacements: Synthesis and Properties, 43rd Annual Meeting, Orthopaedic Research Society, Feb. 9-13, 1997, Sanfrancisco, California, p. 91-16.

Pruitt, Koo, Rimnac, Suresh and Wright, "Compression Fatigue of Ultra High Molecular Weight Polyethylene and its Implications for Total Joint Replacements", 39th Annual Meeting, Orthopaedic Research Society, Feb. 15-18, San Francisco.

R-J Roe, E.S. Grood, R. Shastri, C.A. Gosselin, and F.R. Noyes, Effect of Radiation Sterilization and Aging on Ultrahigh Molecular Weight Polyethylene, Jounal of Biomedical Materials Research, vol. 15, pp. 209-230 (1981).

R. Basheer and M. Dole, Radiation Chemistry of Linear Low-Density Polyethylene. I. Gel Formation and Unsaturation Effects, Journal of Polymer Science: Polymer Physics Edition, vol. 21, pp. 949-956 (1983).

R. Kitamaru et al., "Irridiation Cross Linking of Polyethylene. The Temperature Dependence of Cross Linking in the Crystalline and Amorphous States1", Journal of the American Chemical Society, Vol. 86, pp. 3529-3534 (1964).

R. Shastri, E.S. Grood, R.J. Roe, and F.R. Noyes, Effects of Gamma Radiation Sterilization and In-Vitro Aging on Ultra High Molecular Weight Polyethylene, Proceedings of the 9th Northeast Bioengineering Conference, pp. 419-424 (1981).

R.A. Caputo, Ph.D., et al., Sterilization with Ethylene Oxide and Other Gases, Chemical and Physical Sterilization, pp. 47-64.

R.A. Jones et al., "Radiation-Induced Crosslinking of Polyethylene in the Presence of Acetylene: A Gel Fraction, UV-Visible, and ESR Spectroscopy Study", Journal of Polymer Science: Part B: Polymer Physics, vol. 31, pp. 807-819 (1993).

R.C. Giberson, Oxygen Diffusion and Reaction During g-Irradiation of Polyethyelen, vol. 66, Mar. 1962, pp. 463-468.

R.D. Crowninshield, et al., A Biomechanical Investigation of the Human Hip, J. Biomechanics, 1978, vol. 11, pp. 75-85, Pergamon Press, pp. 75-85.

R.L. Clough and S.W. Shalaby (Eds.), Radiation Effects on Polymers (American Chemical Society 1991).

R.M. Rose, E.V. Goldfarb, E. Ellis, and A.N. Crugnola, Radiation Sterilization and the Wear Rate of Polyethylene, Journal of Orthopaedic Research, vol. 2, pp. 393-400 (1984).

R.M. Streicher, Change in Properties of High Molecular Weight Polyethylenes After Ionizing Irradiation for Sterilization and Modification, Radiation processing for plastics and rubber III, Department of Medical Engineering, Sulzer Brothers Ltd., Winterthur, Switzerland.

R.M. Streicher, "Improving UHMWPE by Ionizing Irradiation Crosslinking During Sterilization", Sulzermedica, Department of Medical Engineering, Winterthur, Switzerland, 17th Annual Meeting of the Society of Biomaterials, May 1-5, 1991.

R.M. Streicher, "Influence of Ionizing Irradiation in Air and Nitrogen for Sterilization of Surgical Grade Polyethylene for Implants," Radiat. Phys. Chem., vol. 31, Nos. 4-6, pp. 693-698, 1988.

R.M. Streicher, "The Behavior of UHMW-PE when Subjected to Sterilization by Ionizing Radiation", Ultra high molecular weight polyethylene as biomaterial in orthopedic surgery, pp. 66-73, 1991.

R.S. Bell, M.D., et al., A Study of Implant Failure in the Wagner Resurfacing Arthroplasty, The Journal of Bone and Joint Surgery, vol. 67-A, No. 8, Oct. 1985, pp. 1165-1175.

R.T. Haslam and Per K. Frolich, Deterioration of Mineral Oils, Industrial and Engineering Chemistry, vol. 19, No. 2, pp. 292-296.

R.W. Hood, et al., Contact Area and Pressure Distribution in Contemporary Total Knee Designs, Department of Biomechanics, The Hospital for Special Surgery, 535 East 70 Street, New York, New York 10021, pp. 233-236.

Radiation Effects on Polymers, American Chemical Society, 1991 (Symposium of Aug. 26-31, 1990) pp. 89-92.

Radical Migration as an Elementary Process in Degradation, Pure and Applied Chem., vol. 55 No. 10, pp. 1595-1601, 1983.

Raffi, "Identifying irradiated foods", Trends in Analytical Chemistry, vol. 17, No. 4, 1998.

Rakita, P.E. And Foure, M, "Gamma Radiation Stabilization of PVC", Journal of Vinyl Technoligy, Jun. 1994, vol. 4, No. 2.

(56) References Cited

OTHER PUBLICATIONS

Ramon B. Gustilo, MD and Roby Thompson, MD, Quadriceps and Patellar Tendong Ruptures following Total Knee Arthroplasty, pp. 41-47.
Ranawat, "The Patellofemoral Joint in Total Condylar Knee asthroplasty: Pros and Cons Based on Five—to Ten-year Follow-uup Observations", Clinical Orthopaedic and Related Research, pp. 93-99.
Reckling et al., "Perfomance Analysis of an ex Vivo Geometric Total Knee Prosthesis" The Journal of Bone and Joint Surgery, pp. 108-112.
Reilly and Martens, "Experimental Analysis of the Quardiceps Muscle Force and Patello-Fimoral Joint Reaction Force for Various Activities", Actaorthop. Scandinav:43:126-137, 1972.
Ricour, Scherer, "Designing Plastic Bearings" SPE Journal, Jul. 1972, vol. 28, pp. 41-45.
Ries, Collis and Lynch, "Seperation of the Polyethylene Liner From Acetabular Cup Metal Backing", Clinical Orthopaedic Related and Research, pp. 166-169.
Ries, M., et al., Abrasive Wear Simulation in Total Knee Arthroplasty, 45th Annual Meeting, Orthopaedic Research Society, Feb. 1-4, 1999, Anaheim, California, p. 853.
Riganakos et al, Effects of ionizing radiation on properties of monolayer and multilayer flexible food packaging materials, Radiation Physics and Chemistry 54 (1999) 527-540.
Ritter, Keating, Faris and Brugo, "Metal-Backed Acetabular Cups in Total Hip Arthoplasty", Journal of Bone and Joint Surgery, vol. 72-A, No. 5, Jun. 1990.
Robert D. Bechenbaugh, M.D. And Duane M. Ilstrup, M.S., Total Hip Arthroplasty, The Journal of Bone and Joint Surgery, vol. 60-A, No. 3, Apr. 1978, pp. 306-313.
Robert G. Westendorf, "A Quantitation Method for Dynamic Headspace Analysis Usingt Multiple Runs", Journal of Chromatography Sciences, vol. 23 Nov. 1985.
Gladius Lewis, Polyethyelen Wear in Total Hip and Knee Arthroplasties, Department of Mechanical Engineering, The University of Memphis, Memphis, Tennessee 38152, Received Dec. 19, 1995; accepted Aug. 9, 1996, pp. 55-75.
Golman, Pruitt, "Comparison of the effects of gamma radiation and low temperature hydroge peroxide gas plasma sterilization on the molecular structure, fatigue resistance, and wear behavior of UHMWPE", Journal Biomed. Mater. Res., 40:378-384, 1998.
Goodacre, Kell, Blanchi, "Neural Networks and Olive Oil" Nature, vol. 359, Oct. 15, 1992, p. 594.
Gordon W. Blunn, Ph.D., et al., The Dominance of Cyclic Sliding in Producing Wear in Total Knee Replacements, Clinical Orthopedics and Related Reasearch, No. 273, Dec. 1991, pp. 253-260.
Greer and Sharp, Comparison of Crosslinked UHMWPE Stabilized by Sequential Annealing or by Remelting, Orthopedic Research Society, Poster No. 1784, 2007.
Grob, Biedermann, "Vaporising Systems for Large Volume Injection or On-line Transfer Into Gas Chromatography: Classification, Critical Remarks and Suggestions" Journal of Chromatography A, vol. 750, pp. 11-23, 1996.
Grob, Jr., G. Grob, K. Grob, "Comprehensive, Standardized Quality Test for Glass Capillary Columns" Journal of Chromatography, vol. 156, pp. 1-20, 1978.
Grunewald and Berger, "Untersuchung der Einwirkung lonisierender Strahlung auf die Gse-und Wasserdampf-Durchlassigkeit von Verpackungs-Folien" Fette Seifen Anstrichmittel, No. 10, pp. 928-934, 1961.
H. Kashiwabara, "ESR Application to Radiation Chemistry of Polymers", Radiat. Phys. Chem., vol. 32, No. 2, pp. 203-208, 1988.
H. Minakawa, et al., Quantification of third-body damage and its effect on UHMWPE wear with different types of femoral head, The Journal of Bone and Joint Surgery, vol. 80-B, No. 5, Sep. 1998, pp. 894-899.
H. Mitsui and F. Hosoi, g-Radiation-Induced Cross-Linking of Polyethylene, Polymer Journal, v. 4, pp. 79-86 (1973).

H. Miyaji et al., "Annealing of nodular linear polyethylene crystallized from the glass", Polymer, 1981, vol. 22, May, pp. 701-703.
H.-P. Hsu, M.D. and Walker, Ph.D., Wear and Deformation of Patellar Components in Total Knee Arthroplasty, Clinical Orthopaedics and Related Research, No. 246, September, 1989, pp. 260-265.
H.Y. Kang, et al., "The Radiation Chemistry of Polyethylene. IX. Temperature Coefficient of Cross-Linking and Other Effects1", Journal of the American Chemical Society/89.9/Apr. 26, 1967, pp. 1980-1986.
Haas, T.W., et al., Crystallinity in Implanted UHMW Polyetheylene, 25th Annual ORS, San Francisco, California, Feb. 20-22, 1979, p. 263.
Haesen et al., "The Effect of Gamma-Irradiation on the Migration Behavior of Organo-tin Additives in PVC" J. of Indust. Irradiation Tech., vol. 1, pp. 259-280, 1983.
Hagman, Jacobsson, "Analysis of Volatile Organic Compounds in Polymers by Dynamic Headspace-Multi-Dimensional Gas Chromatography-Mass Spectrometry" Journal of Chromatography, vol. 395, pp. 271-279, 1987.
Hagman, Jacobsson, "Quantitative Determination of Volatiles in Polyolefins by Dynamic Headspace/Capillary Gas Chromatography/Mass Spectrometry" Journal of Hig Resolution Chromatography, vol. 11, pp. 830-836, Nov. 1988.
Hagman, Jacobsson, "Theoretical Model for Quantitative Determination of Volatile Compunds in Polymers by Dynamic Headspace Sampling" Analytical Chemistry, vol. 61, pp. 1202-1207, 1989.
Hagman, Karlsson, Jacobsson, "Classification of Polymer Batch Variations by Dynamic Headspace/Capillary Gas Chromatography/Multivariate Data Analysis" Journal of High Resolution Chromatography, vol. 11, pp. 46-50, Jan. 1988.
Hagman, Roeraade, "Independently Temperature Programmed Uncoated Precolumn: A concept for Improved Sample Introduction in Capillary GC" J. Microcolumn Separations, vol. 5, No. 4, pp. 341-346, 1993.
Haire, D. Lawrence, et al., "Identification of irradiated foodstuffs: a review of the recent literature," Food Research International, vol. 30, No. 3/4, pp. 249-264, 1997.
Halcomb, Bardos, "Carbon Fiber-Reinforced Polyethylene (CPE) for Total Knee Replacement Prostheses: a Clinical Experience" Medical and Scientific Affairs, vol. XXVII, pp. 364-368, 1981.
Hall, Siney, Unsworth and Wroblewski, "The effect of surface topography of retrieved femoral heads on the wear of UHMWPE sockets", Med. Eng. Phys., vol. 19, No. 8, pp. 711-719, December.
Hamilton, Urian, Greer and Schmidt, "The effect of packaging on the stability of gamma sterilized UHMWPE", 44th Annual Meeting, Orthopaedic Research Society, Mar. 1998.
Hamilton-Kemp et al., "Volatile Compounds from Strawberry Foilage and Flowers" American Chemical Society, pp. 229-239, 1983.
Handlos, "Sterilization by Electron Beam" Radiat. Phys. Chem., vol. 18, No. 1-2, pp. 175-182, 1981.
Hankemeier, Th., et al., "Detectability enhancement by the use of large-volume injections in gas chromatography-cryotrapping-Fourier transform infrared spectrometry," Journal of Chromatography A, 732 (1996) 75-84.
Hanna, "Industrial Problem Solving with UHMW Polyolefins" Hercules, Inc., pp. 1-9.
Harm M van der Vis, et al., Socket wear in ceramic-on-polyethylene total hip arthroplasties, Acta Orthop Scand 1998; 69 (3), pp. 248-252.
Harold Schonhorn, et al., "Surface Crosslinking of Polyethylene and Adhesive Joint Strength", Journal of Applied Polymer Science, vol. 18, pp. 235-243 (1974).
Harris, "The Problem Is Osteolysis", Clinical Orthopaedics and Related Research, No. 311, pp. 46-53, 1995.
Harry E. Figgie, III, M.D., et al., The Influence of Tibial-Patellofemoral Location on Function of the Knee in Patients with the Posterior Stabilized Condylar Knee Prosthesis, The Chondrogenic Potential of Free Autogenous Periosteal Grafts, vol. 68-A, No. 7, Sep. 1986, pp. 1035-1040.
Harry McKellop, Ph.D., et al., Wear of Gamma-Crosslinked Polyethylene Acetabular Cups Against Roughened Femoral Balls, Clinical Orthopaedics and Releated Research, No. 369, pp. 73-82.

(56) References Cited

OTHER PUBLICATIONS

Hastings, Huston, Reber and DiMaio, "Knee Wear Testing of a Radiation Crosslinked and Remelted UHMWPE", 25th Annual Meeting Society for Biomaterials, 1999, p. 328.

Heat of Fusion of Polyethylene, Journal of Polymer Science, vol. 5 (1967) pp. 987-988.

Hedazy, Seguchi, Machi, "Radiation-Induced Oxidative Degradation of Poly(vinyl Chloride" Journal of Applied Polymer Science, vol. 26, pp. 2947-2957, 1981.

Heinze, "Das Verhalten von Hochpolymeren gegenuber energiereicher Strahlung" Kolloid-Zeitschrift und Zeitschrift fur Polymere, Band 210, Heft 1, pp. 45-54.

Helmig, "Artifact-free Preparation, Storage and Analysis of Solid Adsorbent Sampling Cartidges Used in the Analysis of Volatile Organic Compounds in Air" Journal of Chromatography A, vol. 732, pp. 414-417,1996.

Hempel, Rudt, "Bestimmung von Monomeren Fluchtigen Anteilen in Polystyrol und Styrol-Misch-und Pfropfpolymerisaten" Deutsche Lebensmittel-Rundschau, vol. 84, No. 8, pp. 239-242, 1988.

Hernandez, Keating, Faris, Meding and Ritter, "Polyethylene Wear in Uncemented Acetabular Components", Journal of Bone and Related Surgery, vol. 76-B, No. 2, Mar. 1994.

Herzog, Opitz, "Desorption von Athylenoxid aus gassterilisierten Plasten und Elasten" Aus dem Institut fur Allgemeine Hygiene, vol. 25, pp. 386-389, 1979.

Hida, Minemasa, et al., "Determination of triazolam in a drug tablet by thermal desorption gas chromatography," Journal of Chromatography A. 761 (1997) 332-335.

Hideharu Shintani et al, "Analysis of a Carcinogen, 4,4"-Methylenedianiline, from Thermosetting Polyurethane during Sterilzation", Journal of Analytical Toxicology, vol. 13, November/December.

Hideharu Shintani, "Gamma-radiation and autoclave sterilization of thermoplastic and thermosetting polyurethane", pp. 11-28, J. of Radiation Sterilization 1 (1992).

Hill, O'Donnell, Pomery, Sangster, "Radiation Chemical Yields: G Values" pp. 387-397.

Hiller, McCabe, Morabito, "Optimization and Application of the Large Volume On-Column Introduction (LOCI) Techinque for Capillary GC with Preliminary On-Line Capillary Solvent Distillation/Concentration" Journal of High Resloution Chromatography, vol. 16, pp. 5-12, Jan. 1993.

Hodgson, Steven C. et al., "Toward an Optimized Dynamic Headspace Method for the Study of Volatiles in Low-Density Polyethylene," J. Agric. Food Chem., 1998, 46, 1367-1405.

Hoffmann, Bremer, "Design, Performance and Applicability of a Multi-Functional Thermal Desorption System for Trace Analysis in Capillary GC" Gerstel GmbH, pp. 1165-1175.

Hollifield, "Food and Drug Administration Studies of High-Temperature Food Packaging" Food and Packaging Interactions, pp. 22-36.

King, Gsell, Lin, The Residual Free Effect on Aging of Crosslinked Ultra-High Molecular Weight Polyethylene, 25th Annual Meeting Society for Biomaterials, 1999.

Klaassen, Curtis D., "Nonmetallic Environmental Toxicants: Air Pollutants, Solvents and Vapors, and Pesticides," Chapter 70, ZIM-0003211-3232 supplied by The British Library, pp. 1628-1650.

Klaassen, Curtis D., "Principles of Toxicology," Section XVII, Chapter 68, zim-0003234-3246 supplied by The British Library, pp. 1592-1604.

Klarenbeek and van Tongeren, "Viricidal Actions of Ethylene Oxide Gas", pp. 525-528.

Kolb et al., "A Gas Chromatographic Assay for Quantitative Analysis of Volatiles in Solid Materials by Discontinuous Gas Extraction," Chromatographia, vol. 10, No. 12, Dec. 1977, pp. 705-711.

Kolb et al., "Quantitative Analysis of Residual Solvents in Food Packaging Printed Films by Capillary Gas Chromatography with Multiple Headspace Extraction," Journal of Chromatography, 204 (1981) pp. 371-376.

Kolb et al., Quantitative Bestimmung Von Restlosemitteln in Bedruckten Verpackungsfolien Nach Dem Verfahren Der Mehrfach-Gasextraktion, ZIM-0003291-3325 supplied by The British Library, pp. 1-37.

Kolb, et al., "Multiple Headspace Extraction—a Procedure for Quantitative Analysis of Volatile Compounds in Solid Samples and Its Application for the Analysis of Vinyl Chloride Monomer (VCM) and Water in a PVC Resin," ZIM 0003260-3290 supplied by The British Library (Jan. 1981) pp. 2-32.

Koszinowski et al., Deutsche Lebensmittel-Rundschau Zeitschrift fur lebensmittelkunde und Lebensmittelrecht, Deutsche lebensmittel-Rundschau 79, Jahrg., Heft 5, (1983), ZIM-0003326-3330 supplied by The British Library, pp. 179-182.

Kretzschmar, H.-J., Ethylenoxid-Desorption aus sterilisierten Kunststoff- und Gummimaterialien, Ethylene Oxide Desorption from Sterilized Plastic and Rubber materials, Hyg. + Med. 12 (1987 pp. 542-546.

Kurth, Eyerer, Cui, "Effects of Radiation Sterilization on UHMW-Polyethylene" ANTEC 1987, pp. 1193-1197.

Kurth, M., Eyerer, P., and Cui, D., "Effects of Radiation Sterilizaation on UHMW-Polyethyle," The Third World Biomaterials Congress, Apr. 21-25, 1988.

Kurtz et al, "Post-Irradation Aging and the Stressesin UHMWPE Components for Total Joint Replacement", 40th Annual Meeting Orthopaedics Research Society, Feb. 1994.

Kurtz, Muratoglu, Evans, Edidin, "Advances in the Processing, Sterilization, and Crosslinking of Ultra-High Molecular Weight Polyethylene for Total Joint Arthroplasty", Biomaterials 10, pp. 1659-1688, 1999.

Kurtz, Pruitt, Jewett, Foulds and Edidin, "Radiation and chemical crosslinking promote strain hardening behavior and molecular alignment in ultra high molecular weight polyethylene during mutli-axial loading conditions", Biomaterials 20 (1999) 1449-1462.

L. Minkova, et al., Blends of normal high density and ultra-high molecular weight polyethylene, ? irradiated a at a low dose, Colloid & Polymer Science, vol. 268, No. 11, pp. 1018-1023 (1990).

L. Minkova, et al., Blends of normal high density and ultra-high molecular weight polyethylene, ?-irradiated a at a low dose, Colloid & Polymer Science, vol. 268, No. 11, pp. 1018-1023 (1990).

L. Zlatkevich, Improvement in Polypropylene Thermal Ixidative Stability by Annealing Under an Inert Atmosphere, Journal of Polymer Science: Polymer Physics Edition, vol. 23, pp. 2633-2634 (Jul. 1985).

LaBorde, Kimmel, "The Teratogenicity of Ethylene Oxide Administered Intravenously to Mice" Toxicology and Applied Pharmacology, vol. 56, pp. 16-22, 1980.

Lacoste et al., Gamma-, Photo- and Thermally-Initiated Oxidation of Polyolefines Used in Packaging, vol. 15, Nos. 1-2 (1995/1996); pp. 140-152.

Lafortune and Cavanagh, "Three-Dimensional Kinematics of the Patella During Walking", pp. 337-341.

Lancaster, "Estimation of the Limiting PV Relationships for Thermoplastic Bearing Materials" Tribology, May 1971, pp. 82-86.

Landfield, Harold, Sterilization of Medical Devices based on Polymer Selection and Stabilization Techniques, Chapter 43, ZIM-0003350-3374 supplied by The British Library, pp. 975-999.

Langlais et al., "L'intolerance aux debris d'usure des protheses" International Orthopaedics, vol. 4, pp. 145-153, 1980.

Lantos, Peter R., "Plastics in Medical Applications," Journal of Biomaterials Applications, vol. 2 (Jan. 1988), pp. 358-371.

Lanza, "7. Irradiation-Properties Changes", Raychem Corporation, Crystalline Olefin Polymers, pp. 301-358.

Larsen, Thorpe and Armfield, "Oxidation Characteristics of Pure Hydrocarbons", Industrial and Engineering Chemistry, vol. 34, No. 2, pp. 184-193.

Lattimer et al., "Determination of residual volatile chemicals in polymers by solid headspace gas chromatography," ZIM-0003389-3393 supplied by The British Library, (Aug. 1980), pp. 80-88.

Lawrence D. Dorr, M.D., et al., Technical Considerations in Total Knee Arthroplasty, Clinical Orthopaedics and Related Reserach, No. 205, Apr. 1986, pp. 5-11.

Lecon Woo, "Advance Testing Methods for Biomaterials", pp. 91-123 Fundamental Properties and Test Methods.

(56) References Cited

OTHER PUBLICATIONS

Leemhorst, "Industrial Application of the Gamma Sterilization Process" Gammaster BV, pp. 1-8.
Leininger, Mirkovitch, Peters and Hawks, "Change in Properties of Plastics During Implantation", vol. X Trans. Amer. Soc. Artif. Int. Organs, 1964, pp. 320-321.
Letter to the Editors, "Radiation Sterlisation Dose—The Position of the U.K. Panel on Gamma and Electron Irradiation", Radia. Phys. Chem. vol. 29, No. 1, pp. 87-88, 1987.
Levat, McLeod and Freeman, "Why Not Resurface the Patella", The Journal of Bone and Joint Surgery, vol. 65-B, No. 4, Aug. 1983, pp. 448-451.
Lewis, Rorabeck, Bourne and Devane, "Posteromedial Tibial Polyethylene Failure in Total Knee Replacements, "Clinical Orthopaedics and Related Research , No. 299, pp. 11-17, 1994.
Ley, "Radiation Sterilization—Microbiological Aspects" Irradiated Products Limited, pp. 1-16.
Ley, F.J., "the effect of irradiation on packaging materials," J. Soc. Cosmet. Chem. 27 482-489 (1976), pp. 483-489.
Ligon, Woodfin V., Jr. et al., "Device for Thermally-Induced Vapor Phase Transfer of Adsorbed Organics Directly from an Adsorbent to a Gas Chromatograph-Mass Spectrometer," Analytical Chemistry, vol. 48, No. 3, Mar. 1976, pp. 481-484.
Livermore, Ilstrup, Morrey, "Effect of Femoral Head Size on Wear of the Polyethylene Acetabular Component", The Journal of Bone and Joint Surgery, vol. 72-A, No. 4, Apr. 1990, pp. 518-528.
Lombardi et al., "Fracture/Dissociation of the Polyehylene in Metal-Backed patellar Components in Total Knee Arthroplasty" The Journal of Bone and Joint Surgery, vol. 70-A, No. 5, Jun. 1988, pp. 675-679.
Lombardi, Engh, Volz, Albrigo, Brainard, "Fracture/Dissociation of the Polyethylene in Metal-Backed Patellar Components in Total Knee Arthroplatsky", The Journal of Bone and Joint Surgery, vol. 78-A, No. 5, Jun. 1988.
Loy, "Electron Spin Resonance Studies of Free Radical Decay in Gamma-Irradiated Polyethylene" Journal of Polymer Science, vol. XLIV, pp. 341-347, 1960.
Lyarsky et al., "Physicochemical, Toxicological and Hygienic Aspects of Ethylene Oxide Application for the Sterilization of Medical Products" Journal of Hygiene, Epidemiology, Microbiology and Immunology, 32, 1988, No. 3, pp. 257-264.
Lyarsky, Gleiberman, Likhtman, Kopylova, Zayeva, Yurchenko, Kolesnikova, Kareev, "Physicochemical, Toxicological and Hygienic Aspects of Ethylene Oxide Applications for the Sterilization of Medical Products. III. Setting Hygienic Norms in Sterilized Medical Products", Journal of Hygiene, Epidemiology, Microbiology and Immunology, vol. 32, No. 3, pp. 257-264.
Lyons, "Gel Formation in Polyollefins Exposed to Ionizing Radiation" Journal of Polymer Science: Part A, vol. 3, pp. 777-791, 1965.
M. Dole, C. Gupta, and N. Gvozdic, Crystallinity and Crosslinking Efficiency in the Irradiation of Polyethylene, Radiation Physics and Chemistry, vol. 14, pp. 711-720 (1979).
M. Goldman, et al., Characterization of Structure and Fatigue Resistance of Aged and Irradiated UHMWPE, The 21st Annual Meeting of the Society for Biomaterials, Mar. 18-22, 1995, San Fransisco, California.
M. Gvozdic et al., "Kinetics of Free Radical Decay Reactions in Irradiated Isotactic Polypropylene", The Journal of Physical Chemistry, Vol. 85, No. 11, 1981, pp. 1563-1569.
M. Kurth, P. Eyerer, and D. Cui, Effects of Radiation Sterilization on UHMW-Polyethylene, The Third World Biomaterials Congress, Kyoto (Apr. 21-25, 1988).
M. Narkis, et al., "Structure and Tensile Behavior of Irradiation- and Peroxide- Crosslinked Polyethylenes", Journal of Macromolecular Science—Physics, vol. B26, No. 1, 1987, pp. 37-58.
Shintani, Hideharu, Formation and Elution of Toxic Compounds from Sterilized Medical Products: Methylenedianiline Formation in Polyurethane, Journal of Biomaterials Applications, vol. 10—Jul. 1995, pp. 23-58.
Silverman, "Radiation-Induced and Chemcial Crosslinking: A Brief Comparison", pp. 16-22.
Simon et al., "Stiction-Friction' of Total Hip Prosthese and Its Relationship to Loosening" Journal of Bone and Joint Surgery, vol. 57-A, No. 2, pp. 226-230, 1975.
Singh, A., Silverman, J., "Radiation Processing of Polymers," Oxford University Press, New York, (1992), Chapters 1 and 2.
Sir, "irradiation detection", Nature vol. 344, Mar. 15, 1990.
Soudry, Mestriner, Binazzi and Insall, "Total Knee Arthroplatsy Without Patellar Resurfacing", Clinical Orthopaedics and Related Research, No. 205, Apr. 1986.
Spiegelberg, A. et al., "Methods for Routine Control of Irradiated Food: Optimization of a Method for Detection of Radiation-Induced Hydrocarbons and Its Application to Various Foods," Radiat. Phys. Chem., vol. 43, No. 5, pp. 433-444, 1994.
Stanley et al., "Toxicity of Ethylene Oxide Sterilization of Polyvinyl Chloride in Open-heart Surgery" The Journal of Thoracic and Cardiovascular Surgery, Vol. 61, No. 2, pp. 309-314, Feb. 1971.
Steelman, "Ethylene Oxide: The Importance of Aeration", AORN Journal, vol. 55, No. 3, Mar. 1992.
Stefan Oberholzer, et al., New Process Eliminates Wear, Sulzer Technical Review, Mar. 1999, pp. 22-23.
Stephen E. White, MS., et al., Effects of Sterilization on Wear in Total Knee Arthroplasty, Clinical Orthopaedics and Related Research, No. 331, pp. 164-171.
Sun, Stark and Dumbleton, Development of an Accelerated Aging Method for Evaluation of Long-term Irradiation Effects on UHMWPE implants, pp. 969-970.
Sutula, Collier, Saum, Currier B, Currier J, Sandorm, Mayor, Wooding, Sperling, Williams, Kasprzak and Surprenant, "Impact of Gamma Sterilization on Clinical Performance of Polyethylene in the Hip", Clinical Orthopaedics and Related Research, No. 319, pp. 28-40, 1995.
T.F. Williams et al., "Physical and Inorganic Chemistry", Journal of the American Chemical Society, vol. 81, No. 12, Jul. 2, 1959, pp. 2919-2926.
T.P. Schmalzried, et al., Response to Commentary, The Journal of Bone and Joint Surgery, vol. 80-A, No. 8, Aug. 1998, pp. 1242-1243.
Tanzi, Alfonsi, Moscatelli, Cigada, "Sterilization Effects on highly crosslinked UHMWPE", Society for Biomaterials, 25th Annual Meeting, p. 213, 1999.
The Fracture of Ultrahigh Molecular Weight Polyethylene in the Human Body, Journal of Biomedical Materials Research, vol. 13, pp. 669-672.
Tompkins and Cantwell, "The Use of Ethylene Oxide to Inactivate Insect Viruses in Insectaries", Journal of Invertebrate Pathology, vol. 25, 139-140 (1973).
Trainor, Haward, Hay, "The effect of Density on the Properties of High Molecular Weight Polyethylenes", Journal of Polymer Science, vol. 15, 1077-1088, (1977).
Trent, Walker, "Wear and Conformity in Total Knee Replacement" Wear, vol. 36, pp. 175-187, 1976.
Uchida, Yoshino, Doi and Kudo, "Side-effects of Prosthetic Materials on the Human Body", International Orthpaedics vol. 3, 285-291 (1980).
Ungar, "Review Radiation Effects in Polyethylene and n-alkanes" Journal of Materials Science, vol. 16, pp. 2635-2656, 1981.
Ungethum, Hinterberger, "Der Einflub der Strahlensterilisation auf das Verschleibverhalten von Polyathylen" Z. Orthop. vol. 117, pp. 790-794, 1979.
V.K. Knyazev ad I.A. Sidorov, Irradiated Polyethylene in Engineering (Khimiya 1974).
Vagn Handlos, The Hazards of ethylene oxide sterilization, Arch. Pharm. Chemi, Sci. Ed. 7, 1979, pp. 147-157.
van Lieshout, Mark H.P.M. et al., "Characterization of Polymers by Multi-Step Thermal Desorption/Programmed Pyrolysis Gas Chromatography Using a High Temperature PTV Injector," J.High Resol. Chromatogr., vol. 19, Apr. 1996, pp. 193-198.
Van Lieshout, Mark P.M. et al., "Programmed-temperature vaporiser injector as a new analytical tool for combined thermal desorption-pyrolysis of solid samples, Applicaton to geochemical analysis," J. Chromatogr. A 764 (1997) 73-84.

(56) References Cited

OTHER PUBLICATIONS

Varner et al., "Packing Materials,—Determination of Benzene in Polypropylene Food-Packaging Materials and Food-Contact Paraffin Waxes", J. Assoc. Off. Anal. Chem. (vol. 74, No. 2 , 1991).

Vesa O Saikko, Wear of the Polyethylene Acetabular Cup, Acta Orthop Scand 1995; 66 (6), pp. 501-506.

Vesa Saikko, Tinna Ahlroos, Wear Simulation of UHMWPE for total hip replacement with a multidirectional motion pin-on-disk device: Effects of counterface material, contact area, and lubricant, May 18, 1999, pp. 147-154.

Vince and Dorr, "Surgical Technique of Total Knee Arthroplasty: Principles and Controversy", Techniques Orthop. 1987:1(4):69-82.

W.G. Perkins, et al., "Effect of Gamma Radiation and Annealing on Ultra-Oriented Polyethylene", Polymer Engineering and Science, Mid-May, 1978, vol. 18, No. 6, pp. 527-532.

Walker, Ben-Dov, Askew, Pugh "The Deformmation and Wear of Plastic Components in Artificial Knee Joints—an Experimental Study," MEP Ltd. 1981, vol. 10, pp. 33-38.

Walker, Hsieh, "Conformity in Condylar Replacement Knee Prostheses" The Journal of Bone and Joint Surgery, vol. 59-B, No. 2, pp. 222-228, May 1977.

Wallin, Richard F., "Meeting Report—Global Biocompatibility," Medical Device Technology, May 1995, pp. 34, 36, 38.

Wang et al., "Wear, Oxidation and Mechanical Properties of a Sequentially Irradiated and Annealed UHMWPE in Total Joint Replacement", J. Phys. D: Appl. Phys. 39, pp. 3213-3219, 2006.

Warty, Sauer, Charlesby, "Effects of Radiation and Chain Ends on Fatigue Behaviour of Polystyrene" European Polymer Journal, vol. 15, pp. 445-452.

Webb, Wright, Winter, "The Monk "Soft Top" Endoprosthesis" The Journal of Bone and Joint Surgery, vol. 62-B, No. 2, May 1980, pp. 174-179.

Weightman and Light, "A comparison of RCH 1000 and Hi-Fax 1900 Ultra-high Molecular weight polyethylenes", Biomaterials, vol. 6, May 1985, pp. 177-183.

Weightman, Paul, Rose, Simon, Radin, "A Comparative Study of Total Hip Replacement Prostheses" J. Biomechanics, 1973, vol. 6, pp. 299-311.

Weightman, Simon, Paul, Rose, Radin, "Lubrication Mechanism of Hip Joint Replacement Prostheses" Journal of Lubrication Technology, Apr. 1972, pp. 131-135.

Weightman, Swanson, Isaac and Wroblewski, "Polyethylene Wear From Retrieved Acetabular Cups", The Journal of Bone and Joint Surgery, vol. 73-b, No. 5, Sep. 1991, pp. 806-810.

Whitbourne, Mogenhan, Ernst, Determination of 2-Chloroethanol in Surgical Materials by Extraction and Gas Chromatography, Journal of Pharmaceutical Sciences, vol. 58, Aug. 1969, pp. 1024-1025.

Willert, Semlitsch, "Reaction of the Articular Capsule to Plastic and Metallic Wear Products from Joint Endoprostheses" Sulzer Technical Review, Feb. 1975, pp. 119-133.

Willert, Semlitsch, "Reactions of the Articular Capsule to Wear Products of Artificial Joint Prostheses" J. Biomed. Mater. Res., Vol. 11, pp. 157-164.

Williams, Mayor and Collier, "The Impact of Sterilization Method on Wear in Knee Artrhoplasty", Clinical Orthopaedics and Related Research, No. 356, pp. 170-180, 1998.

Winarno and Stumbo, "Mode of Action of Ethylene Oxide on Spores of Clostridium Botulnum 62A", Journal of Food Science, vol. 36, 1971.

Winslow, Hellman, Matreyek and Stills, "Autoxidation of Semicrystalline Polyethylene", Polymer Engineering and Science, Jul. 1966, pp. 273-278.

Winslow, Matreyek, Stills, "Oxidative Embrittlement of Polyethylene" Bell Telephone Laboratories, Inc., Division of Polymer Science, pp. 304-315.

Woolson, Steven T., et al., "Wear of the Polyethylene of Harris-Galante Acetabular Components Inserted without Cement," The Journal of Bone and Joint Surgery, Incorporated., vol. 77-A, No. 9, Sep. 1995.

Robert M. Streicher, "Investigation on Sterilization and Modification of High Molecular Weight Polyethylenes by Ionizing Irradiation," Reprint from beta-gamma Jan. 1989, beta-gamma Jan. 1989, pp. 34-43.

Robert M. Streicher, "Investigation on Sterilization and Modification of High Molecular Weight Polyethylenes by Ionizing Irradiation," Reprint from beta-gamma Jan. 1989, beta-gamma Jan. 1989, pp. 34?43.

Robert M. Streicher, "Ionizing Irradiation for Sterilization and Modification of High Molecular Weight Polyethylenes," Plastics and Rubber Processing and Applications, vol. 10, No. 4, 1988, pp. 221-229.

Roe, Grood, Shastri, Gosselin, Noyes, "Effect of Radiation Sterilization and Aging on Ultrahigh Molecular Weight Polyethylene" Journal of Biomedical Materials Research, vol. 15, 1981, pp. 209-230.

Roe, Ryong-Joon, Grood, Edward S., Shastri, Ranganath, Gosselin, Cynthia A., and Noyes, Frank R., "Effect of Radiation Sterilization and Aging on Ultrahigh Molecular Weight Polyethylene," Journal of Biomaterials Research, vol. 15, 209-230 (1981).

Roffman, Hirsh and Mendes, "Fracture of the Resurfaced Patella in Total Knee Replacement", Clinical Orthopaedic and Related Research, No. 148, May 1980.

Roger W. Hood, et al., Retrieval analysis of total knee prosthesis: A method and its application to 48 total condylar prostheses, Journal of Biomedical Materials Research, vol. 17, 829-842 (1983), pp. 829-842.

Rose et al., "A Method for the Quantitative Recovery of Polyethylene Wear Debris From the Simulated Service of Total Joint Prostheses" Wear, vol. 51, pp. 77-84, 1978.

Rose et al., "On the Origins of High in Vivo Wear Rates in Polyethylene Components of Total Joint Prostheses" Clinical Orthopaedics and Related Research, No. 145, pp. 277-286, 1979.

Rose et al., "On the True Wear Rate of Ultra High-Molecular-Weight Polyethylene in the Total Hip Prosthesis" The Journal of Bone and Joint Surgery, Inc., vol. 62A, No. 4, Jun. 1980, pp. 537-549.

Rose et al., "The Effect of Ionizing Radiation on Ultra High Molecular Weight Polyethylene" Transactions of the 3rd Annual Meeting of the Society for Biomaterials, pp. 117, 1977.

Rose, Goldfarb, Ellis, Crugnola, "On the Pressure Dependence of the Wear of Ultrahigh Molecular Weight Polyethylene" Wear, vol. 92, pp. 99-111, 1983.

Rose, Goldfarb, Ellis, Crugnola, "Radiation Sterilization and the Wear Rate of Polyethylene" Journal of Orthopaedic Research, vol. 2, No. 4, pp. 393-400, 1984.

Rose, Ries, Paul Crugnola, Ellis, "On the True Wear Rate of Ultrahigh Molecular Weight Polyethylene in the Total Knee Prothesis" Journal of Biomedical Materials Research, 1984, vol. 18, pp. 207-224.

Rose, William P., "Determining Volatile Extractives from Micro Susceptor Food Packaging", Chapter 6, Americal Chemical Society, 1991.

Rostoker, "Some New Studies of the Wear Behavior of Ultrahigh Molecular Weight Polyethylene", Journal of Biomed, vol. 10, pp. 303-310 (1976).

Rostoker, Galante, "Contact Pressure Dependence of Wear Rates of Ultra High Molecular Weight Polyethylene" Journal of Biomedical Materials Research, vol. 13, pp. 957-964, 1979.

S. Bhambri, et al., A Comparison of Morphology of Hip Simulator and Pin-On-Flat Wear Particles of Highly Crosslinked Polyethylene, 1999 Society for Biomaterials, 25th Annual Meeting Transactions, pp. 505, 211 and 497.

S. Shimada et al., "Relation between diffusion controlled decay of radicals and ?-relaxation in polyethylene and polyoxymethylene", Polymer, vol. 20, 404 (1979).

S.K. Bhateja and E.H. Andrews, Thermal, Mechanical, and Rheological Behavior of Blends of Ultrahigh and Normal-Molecular-Weight Linear Polyetheylenes, Polymer Engineering and Science, Nov. 1983, vol. 23, No. 16, pp. 888-894.

S.K. Bhateja, Changes in the crystalline content of irradiated linear polyethylenes upon ageing, Polymer, 1982, vol. 23, May, pp. 654-655.

S.K. Bhateja, Uniaxial tensile creep behaviour of ultra high molecular weight linear polyethylene, Polymer, 1981, vol. 22, January, pp. 23-28.

(56) References Cited

OTHER PUBLICATIONS

S.K. Bhateza, Radiation-Induced Crystallinity Changes in Linear Polyethylene: Influence of Aging, Journal of Applied Polymer Science, vol. 28, pp. 861-872 (1983).
S.S. Grewel and P.W. Jackson, Electrochemical Machining of Orthopaedic Components, Advances in Manufacturing Technology, pp. 366-373.
Salovey and Shinde, "Irradiation of Ultra High Molecular Weight Polyethylene", Departments of Chemical Engineering and materials Science, USC, pp. 113-119.
Salovey, Shinde, "Irradiation of Ultra High Molecular Weight Polyethylene" Departments of Chemical Engineering and materials Science, USC.
Salvati, Wright, Burstein, Jacobs, "Fracture of Polyethylene Acetabular Cups" Journal of Bone and Joint Surgery, vol. 61-A, No. 8, pp. 1239-1242, 1979.
Sanford and Saum, "Accelerated Oxidative Aging Testing of UHMWPE", 41st Annual Meeting Orthopaedic Research Society, Feb. 1995.
Saum, "Oxidation vs. Depth and Time for Polyethylene Gamma Sterilized in Air", 40th Annual Meeting, Orthopaedic Society, Feb. 21-24, 1994.
Savan, "The Sterilzing Action of Gaseous Ethylene Oxide on Foot-and-Mouth Disease Virus", American Journal Vet. Res., Jan. 1955.
Schaudy, "Oxidation Processes in the Radiation-induced Cross-linking of Low Density Polyethylene" German Plastics, pp. 22-25, 1978.
Schmalzried, Guttmann, Grecula and Harlan, "The relationship between the design, position and articular wear of acetabular components inserted without cement and the development of pelvic osteolysis", Journal of Bone and Joint Surgery, vol. 76-A, No. 5, May 1994.
Schmalzried, Jasty, Harris, "Periprostetic Bone Loss in Total Hip Arthroplasty: Polyethylene Wear Debris and the Concept of the Effective Joint Space", Journal of Bone and Joint Surgery, vol. 74-A, No. 6, Jul. 1992.
Schmidt and Blomberg, L., Dynamic Headspace Enrichment/Reinjection for Open Tubular GC/FTR Analysis of Volatiles in Polymers, Journal of High Resolution Chromography & Chromatography Communications, 1988.
Schnabel, "Linear-Energy-Transfer Effects on Polymers" 1991 American Chemical Society.
Schulzki et al, "Detection of Radiation-Induced Hydrocarbons in Camembert Irradiated before and after the Maturing Process-Comparison of Florisil Column Chromatography and On-Line Coupled Liquid Chromatography-Gas Chromatography", Journal of Agricul-ture Food Chemistry, 1995, 43, 372-376.
Schulzki, G. et al., "Irradiation Detection in Complex Lipid Matrices by Means of On-Line Coupled (LC-)LC-GC,"BgVV—Federal Institute for Health Protection of Consumers and Veterinary Medicine, Berlin, Germany (ZIM-0003749-3758).
Schulzki, G., et al., "Detection of Radiation-Induced Hydrocarbons in Irradiated Fish and Prawns by Means of On-Line Coupled Liquid Chromatography-Gas Chromatography," J. Agric. Food Chem. 1997, 45, 3921-3927.
Scott, "Prosthetic Replacement of the Patellofemoral Joint", Orthopedic Clinics of North America, vol. 10, No. 1, Jan. 1979.
Seedhom and Terayama, "Knee forces during the activity of getting out of a chair with and without the aid of arms", Biomedical Engineering, Aug. 1976.
Serekian, Bruchalski, Manley, "The peformance of irradation-crosslinked UHMWPE cups under abrasive conditions throughout hip joint simulation wear testing", 45th Annual Meeting, Orthopaedic Research Society, Feb. 1999.
Shadrake, Guiu, "Interactions Between Cross-links and Dislocations in Polyethylene Crystals: a Model of Irradiation Hardening" Journal of Materials Science, vol. 17, pp. 145-156,1982.
Sharpe, P.H.G, "Dosimetry for Food Irradiation", Food Irradiation and the Chemist pp. 109-123.

Shastri, Grood, Roe, Noyes, "Effect of Aging on Ultra High Molecular Weight Polyethylene" Department of Orthopaedic Surgery, University of Cincinnati Medical Center, pp. 16-18.
Shen and McKellop, "The Crosslinked Ultra-High Molecular Weight Polyethylene", The J Vernon Luck Orthop Research Center, Orthopaedic Hospital, UCLA, 2002.
Shen F-W., et al., Improving the Resistance to Wear and Oxidation of Acetabular Cups of UHMWPE by Gamma Radiation Crosslinking and Remelting, 24th Annual Meeting of the Society for Biomaterials, Apr. 22-26, 1998, San Diego, California, U.S.A., p. 3.
Shen, Dumbleton, "The Friction and Wear Behavior of Irradiated Very High Molecular Weight Polyethylene" Wear, vol. 30, pp. 349-364, 1974.
Shen, Jacob,"Aid for Analytical Chemists—In-Site Sampling System for Thermal Volatilization Analysis of Nonvolatile Materials by Gas Chromatography-Mass Spectrometry", Analytical Chemistry, vol. 48, No. 8, May 1977.
Shigetaka' Shimada et al., "Free radicals trapped in polyethylene matrix: 2. Decay in single crystals and diffusion", Polymer, vol. 18, No. 25, (1977).
Shin Tsuge et al, "Development of a New Pyrolyzer for thermal Desorption and/or Pyrolysis Gas Chromatography of Polymeric Materials"pp. 269-272 Journal of High Resolution Chromatography.
A. Brent Bankston, MD., et al., Polyethylene Wear in Total Hip Arthroplasty, Clinical Orthopaedics and Related Research, No. 317, pp. 7-13.
A. Chapiro, Physical and Chemical Effects of Ionizing Radiations on Polymeric Systems, pp. 367-374.
A. Charlesby and S.H. Pinner, Analysis of the Solubility Behaviour of Irradiated Polyethylene and Other Polymers, Proceedings of the Royal Society of London: A, pp. 367-386 (1959).
A. Charlesby, "The effects of ionising radiation on polymers", Irradiation Effects on Polymers, pp. 49-59, 1991.
A. Charlesby, Proceedings of the Royal Society of London: A, vol. 215, p. 187 (1952).
A. Venema, "Dynamic Headspace Capillary Gas Chromatography: A Versatile Analytical Technique" , pp. 128-131, Journal of High Resolution Chromatography & Chromatography Communications.
A. Venema, Possibilities of Dynamic Headspace Analysis Coupled with Capillary GC for the Investigation of Solid Samples, pp. 637-640, Journal of High Resolution Chromatography & Chromatography Communications.
A. Wang, et al., Lubrication and wear of ultra-high molecular weight polyethylene in total joint replacements, Tribology International, vol. 31, Nos. 1-3, pp. 17-33, 1998.
A. Wang, et al., The Impact of Lubricant Protein Concentration on the Outcome of Hip Joint Simulator Wear Testing, 1999 Society for Biomaterials, 25th Annual Meeting Transactions, p. 178.
A.M. Rijke and L. Mandelkern, Irradiation of Linear Polyethylene, Partitioning between Sol and Gel, Macromlecules, vol. 4, pp. 594-599 (1971).
A.R. Champion, Fatigue Crack Growth Behavior of Enhanced Ultra-High Molecular Weight Polyethyelen, The 20th Annual Meeting of the Society for Biomaterials, Apr. 5-9, 1994, Boston, MA, USA, p. 76.
Akeharu Tsuruta et al., "Annealing of Ultra-Oriented High Density Polyethylene Extrudates", Polymer Engineering and Science, Jun. 1983, vol. 23, No. 9, pp. 521-529.
Albert H. Burstein, Biomechanics of the Knee, pp. 21-39.
Alberto Sturaro et al, "Identification of low-boiling products in the polyetyrene matrix" Annali di Chimica, 81, 1991, by Societa Chimica Italiana.
Aldo M. Crugnola, et al., Ultrahigh Molecular Weight Polyethyelen as Used in Articular Prostheses (A Molecular Weight Distribution Study), Journal of Applied Polymer Science, Vol. 20, (1976) pp. 809-812.
Allen, Brooks, Unwin, McGuinness, "Studies of the Degradation of Organotin Stabilizers in Poly(vinyl Chloride) During Gamma Irradiation" Applied Organic Chemistry, pp. 311-317, 1987.
Allen, Clench, Crowson, Leathard, "Characterisation of Solvent-Extractable Transformation Products of High Molecular Weight Hin-

(56) References Cited

OTHER PUBLICATIONS dered Phenols in Polypropylene Subjected to Ionising Radiation in Air or to Thermal Ageing" Polymer Degradation and Stability, vol. 39, pp. 293-297, 1993.
Allen, Clench, Crowson, Leathard, "Identification by Particle-beam Liquid Chromatography—Mass Spectrometry of Transformation Products of the Antioxidant Irganox 1330 in Food-Contact Polymers Subjected to Electron-Beam Irradiation" Journal of Chromatography, vol. 629, pp. 283-290, 1993.
Allen, Crowson, Leathard, "A Comparison of the Effects of Gamma and Electron-beam Irradiation on Antioxidants Present in Food-contact Polyolefins" Chemistry & Industry, Jan. 1990, pp. 16-17.
Allen, Crowson, Leathard, Smith, "The Effects of Ionising Radiation of Additives Present in Food-contact Polymers" Food Irradiation and the Chemist, pp. 124-139.
Allen, Leathard, Smith, "Effects of Gamma-Irradiation on Hindered Phenol Antioxidants in Poly(vinyl Chloride) and Polyolefins" Chemistry and Industry, pp. 198-199, Mar. 1987.
Allen, Leathard, Smith, "Gamma-irradiation of Food Contact Plastics: The Rapid Destruction of an Arylphosphite Antioxidant in Polypropylene" Chemistry and Industry, pp. 854-855, Dec. 1987.
Allen, Leathard, Smith, "The Effects of Gamma Irradiation of Food Contact Plastics on the Extent of Migration of Hindered Phenol Antioxidants Into Fatty Food Simulants" Chemistry and Industry, Jun. 1988, pp. 399-400.
Allen, Leathard, Smith, "The Effects of Gamma Irradiation of the Fate of Hindered Phenol Antioxidants in Food Contact Polymers. Analytical and 14C-Labelling Studies" Radiat. Phys. Chem., vol. 38, No. 5, pp. 461-465, 1991.
Allen, Leathard, Smith, "The Unexpected Degradation of an Internal Standard in the H.P.L.C. Determination of Anti-oxidants in Gamma-irradiated Food Contact Polyolefins: a Possible Basis for a Chemical Test for an Irradiated Plastic" Chemistry and Industry, Jan. 1989, pp. 38-39.
Allen, Leathard, Smith, McGuinness, "The Effects of Gamma Irradiation on the Fate of Polymer Additives and the Implications for Migration From Plastic Food Contact Materials" Food Additives and Contaminants, vol. 5, Supp. No. 1, pp. 433-435, 1988.
Amstutz et al., "Implant Wear: The Future of Total Joint Replacement" Symposium, Sep. 1995.
Amstutz, "Biomaterials for Artificial Joints" Orthopedic Clinics of North America, vol. 4, No. 2, Apr. 1973, pp. 235-248.
Amstutz, "Polymers as Bearing Materials for Total Hip Replacement: A Friction and Wear Analysis" Journal of Biomedical Materials Research, vol. 3, pp. 547-568, 1968.
Amstutz, Lodwig, "Wear of Polymeric Bearing Materials: The Effects of in Vivo Implantation" Journal of Biomedical Materials Research, vol. 10, pp. 25-31, 1976.
Andrea Cracchiolo III, et al., A Prospective Comparative Clinical Analysis of the First-Generation Knee Replacements: Polycentric vs. Geometric Knee Arthroplasy, Clinical Orthopaedics and Related Research, No. 145, Nov.-Dec. 1979, pp. 37-46.
Andrew G. Urquhart, et al., Polyethylene Wear After Total Hip Arthroplasty: The Effect of a Modular Femoral Head with an Extended Flange-Reinforced Neck, The Journal of Bone and Joint Surgery, vol. 80-A, No. 11, Nov. 1998, pp. 1641-1647.
Ann F. Booth, Industrial Sterilization Technologies: New and Old Trends Shape Manufactuer Choices, Medical device and Diagnostic Industry, Supplied by The British Library , pp. 64-72.
Artandi, "Successful and Promising Applicaitons of Radiation Processing—Sterilization" Radiat. Phys. Chem., vol. 9, pp. 183-191, 1977.
Atkinson, Brown, Dowson, "The Wear of High Molecular Weight Polyethylene" Transactions of the ASME, vol. 100, pp. 208-218, 1978.
Azuma et al., "Effects of Film Variety on the Amounts of Carboxylic Acids from Electron Beam Irradiated Polyethylene Film" Agric. Biol. Chem., vol. 48, pp. 2003-2008, 1984.

Azuma et al., "Effects of the Conditions for Electron Beam Irradiation of the Amounts of Volatiles from Irradiated Polyethylene Film" Agric. Biol. Chem., vol. 48, pp. 2009-2015, 1984.
Azuma et al., "Identification of the Volatiles from Low Density Polyethylene Film Irradiated with an Electron Beam" Agric. Biol. Chem., Vol. 47, pp. 855-860, 1983.
B.J. Livingston, M.D., et al., Complications of Total Hip Arthroplasty Associated with the Use of an Acetabular Component with a Hylamer Liner, The Journal of Bone and Joint Surgery, vol. 79-A, No. 10, Oct. 1997, pp. 1529-1538.
Baker, Hastings and Pruitt, "Compression and tension fatigue resistance of medical grade ultra high molecular weight polyethylene: the effect of morphology, sterilization, aging and temperature", Polymer 41 (2000) 795-808.
Barbara H. Currier, et al., Effect of Fabrication Method and Resin Type on Performance of Tibial Bearings, 2000 John Wiley & Sons, Inc., pp. 143-151.
Barbara H. Currier, ME, et al., Shelf Life and In Vivo Duration, Clinical Orthopaedics and Related Research, No. 342, 1997 Lippincott-Raven Publishers, pp. 111-122.
Bargmann et al, "Current Sterilization and Packaging Methods for Polyethylene", Clinical Orthopaedics and Related Research, No. 369, pp. 49-58, 1999.
Barrett, "Dosimetry with Dyed and Undyed Acrylic Plastic" Int. J. Appl. Radiat. Isot., vol. 33, pp. 1177 to 1187, 1982.
Bartel, Bicknell, Wright, "The Effect of Conformity, Thickness, and Material on Stresses in Ultra-High Molecular Weight Components for Total Joint Replacement" The Journal of Bone and Joint Surgery, vol. 68-A, No. 7, Sep. 1986, pp. 1041-1051.
Bartel, Wright, Edwards, "The Effect of Metal Backing on Stresses in Polyethylene Acetabular Components" pp. 229-239.
Beenen, Polva, "Practical Problems in Radiatio Sterilization of Medical Devices Made From Plasticized PVC" Radiat. Phys. Chem., vol. 35, Nos. 1-3, pp. 364-368, 1990.
Bennett, A.P., Wright, T.M., Li,S., Global Reference UHMWPE: Characterization and Comparison to Commercial UHMWPE, 42nd Annual Meeting, Orthopedic Research Society, Feb. 19-22, 1996, Atlanta, Georgia, p. 472.
Bersch, Stromberg, Achhammer, "Effect of Radiation on Plastic Films" Technical & Engineering, Aug. 1959, pp. 117-121, 166, 168.
Biedermann, Maurus, et al., "Polyimide for deactivating gas chromatography vaporising chambers and fixing packing materials," Journal of Chromatography A, 764 (1997) 65-71.
M.A. Ikokwu, et al., The Use of Ultrahigh Molecular Weight Polyethylene in Articular Prosthesis—IV. Environmental Stress Cracking Propensity of Polyethylene in Bovine Serum, pp. 366-371.
M.A.R. Freeman, M.D., Freeman-Samuelson total Arthroplasty of the Knee, Clinical Orthopaedics and Related Research, No. 192, Jan.-Feb., 1985, pp. 46-58.
M.B. Berry, et al., The Use of Ultrahigh Molecular Weight Polyethylene in Articular Prosthesis—I Polymer Characterization of Six "Off the Shelf" Acetabular Components, ORPL.
M.P.G. Bostrom, A.P., et al., Degradation in Polyethyelene As a Result of Sterilization, Shelf Storage, and IN VIVO Use, 40th Annual Meeting, Orthopaedic Research Society, Feb. 21-24, 1994, New Orleans, Louisiana, p. 288.
M.S. Jahan et al., "Effect of Post-Irradiation Storage Condition on Thermoluminescence From Ultra-High Molecular Weight Polyethylene", Journal of Luminescence, 40 & 41 (1988), pp. 242-243.
M.S. Jahan, et al., "Combined Chemical and Mechanical Effects on Free Radicals in UHMWPE Joints During Implantation", Journal of Biomedical Materials Research, vol. 25, pp. 1005-1017, (1991).
Mack L. Clayton, M.D., Patellar Complications after Total Condylar Arthroplasty, Clinical Orthopaedics and Related Research, No. 170, Oct. 1982, pp. 152-155.
Malek, Euliano, Krankovitch, Cole, "Geometric Total Knee Prosthesis" Orthopaedic Review, vol. VIII, No. 6, Jun. 1979, pp. 67-73.
Manley, Serekian, "Wear Debris: An Environmental Issue in Total Joint Replacement", Clinical Orthopaedics and Related Research, No. 298, pp. 137-146, 1994.
Mark and Curro, "Improvement in Polypropylene Thermal Oxidative Stability by Annealing Under an Inert Atmosphere", Journal of Polymer Science, vol. 23, pp. 2633-2634, 1985.

(56) References Cited

OTHER PUBLICATIONS

Marqué, D. et al., "Migration of plastic packaging light stabilizers into food simulators: their reactivity in unsaturated fatty esters," J. Chim. Phys. (1994) 91, 1890-1895.
Marrs H. Barton, D.C., et al., Comparative Wear Under Three Different Tribological Conditions of Acetylene Crosslinked Ultra High Molecular Weight Polyethylene, 44th Annual Meeting, Orthopaedic Research Society, Mar. 16-19, 1998, New Orleans, Louisiana.
Martin Hudis, "Surface Crosslinking of Polyethylene Using a Hydrogen Glow Discharge", Journal of Applied Polymer Science, vol. 16, pp. 2397-2415 (1972).
Marylyn Bakker, Editor-in-chief, The Wiley Encyclopedia of Packaging Technology, 1986, pp. 530, 562, 564.
Masaru Matsuo, et al., "Cross-Linking of Ultrahigh Molecular Weight Polyethylene Films Produced by Gelation/Crystallization form Solution under Elongation Process", Macromolecules, vol. 19, No. 7, Jul. 1986, pp. 2028-2035.
Masayoshi Furuhashi and Takuyuki Miyamae, Ethylene Oxide Sterilization of Medical Devices—With Special Reference to the Sporicidal Activity and Residual Concentration of Ethylene Oxide and Its Secondary Products, Bull. Tokyo Med. Dent. Univ., 29: (1982) pp. 23-35.
Mathews and Hofstad, "The Inactivation of certain Animal Viruses by Ethylene Oxide", Carbide and Carbon Chemicals Corporation, pp. 452-461.
McIntyre, Dale C. et al., "Development of High Sensitivity Techniques for Characterizing Outgassing of Polymeric Construction Materials for Microenvironments," Proceedings—Institute of Environmental Sciences, 1984, pp. 474-480.
McKeelop, Clarke, Markolf and Amstutz, "Wear Characteristics of UHMW Polyethylene: A Method for Accurately Measuring Extremely Low Wear Rates", Journal of Biomedical Materials Research, vol. 12, pp. 895-927 (1978).
McKellop, Griffin, Clarke, Markolf, "Increased WEar of UHMW Polyethylene After Gamma Radiation Sterilization" 26th Annual ORS, Feb. 5-7, 1980, p. 99.
McKellop, Shen, Lu, Cammpbell and Salovey, "Development of an Extremely Wear-Resistant Ultra High Molecular Weight Polyethylene for Total Hip Replacements", Journal of Orthopaedic Research 17:157-167, 1999.
McKellop, Shen, Lu, Campbell and Salovey, "Development of an Extremely Wear-Resistant Ultra High Molecular Weight Polyethylene for Total Hip Replacements", Journal of Orthopaedic Research, The Jounal of Bone and Joint Surgery, 17, pp. 157-167, 1999.
McLain, Bargar, "The Effect of Total Knee Design on Patellar Strain" The Journal of Arthroplasty, vol. 1, No. 2, Jun. 1986, pp. 91-98.
McLaren, Tabor, "The Friction and Deformation Properties of Irradiated Polytetrafluoroethylene (PTFE)" Wear, vol. 8, pp. 3-7, 1965.
McLaughlin, "Radiation Processing Dosimetry" Radiat. Phys. Chem., vol. 21, No. 4, pp. 359-366, 1983.
Merkow, Soudry, Insall, "Patellar Dislocation following Total Knee Replacement", Journal of Bone and Joint Surgery, vol. 67-A, No. 9, Dec. 1985.
Michael D. Ries, MD., et al., Early Delamination of a Hylamer-M Tibial Insert, The Journal of Arthroplasty, vol. 11, No. 8, 1996, pp. 974-976.
Michael G. Tanner, BS., et al., Effect of Polyethylene Quality on Wear in Total Knee Arthroplasty, Clinical Orthopaedics and Related Research, No. 317, pp. 83-88.
Michael Szycher, Ph.D., "High Performance Biomaterials—A comprehensive guide to medical and pharmaceutical applications".

Michaels and Strumbo, "Ethylene Oxide Steriliztion of Salmonella Senftenberg and *Escherichia Coli*: Death Kinetics and Mode of Action", Journal of Food and Science, vol. 35 (1970) pp. 631-634.
Miller et al., "A Comparative Evaluation of the Wear of Ultra-High Molecular Weight Polyethylene Abraded by Ti-6AI-4V" Wear, vol. 28, pp. 207-216, 1974.
Mirra, Amstutz, Matos, Gold, "The Pathology of the Joint Tissues and its Clinical Relevance in Prosthesis Failure" Clinical Orthopaedics and Related Research, No. 117, pp. 221-240, 1976.
Mol, Hans G.J., et al., "Trace level analysis of micropollutants in aqueous samples using gas chromatography with on-line sample enrichment and large volume injection," Journal of Chromatography A, 703 (1995) 277-307.
Morales, Aparicio, Rios, "Dynamic Headspace Gas Chromatographic Method for Determining Volatiles in Virgin Olive Oil", Journal of Chromatography, 66a (1994) 455-462.
Morrison, "The Mechanics of the Knee Joint in Relation to Normal Walking" J. Biomechanics, vol. 3, pp. 51-61, 1970.
Munari, Colombo, Magni, Zilioli, Trestianu, "GC Instrumentation for On-Column Injection of Large Volumes: Automated Optimization of Conditions", Journal of Microcolumn Seperations 7(4):403-409, 1995.
Muratoglu, Bragdon, O'Connor, Jasty and Harris, "A Novel Method of Cross-Linking Ultra-High Molecular-Weight Polyethylene to Improve Wear, Reduce Oxidation, and Retain Mechanical Properties", Journal of Arthroplasty, vol. 16, No. 2, 2001, pp. 149-160.
Muratoglu, McGarry, Bragdon, Jasty and Harris, "The effect of peroxide content on the cross-link density, mechanical properties and wear behavior of UHMWPE", 44th Annual Meeting, Ortopaedic Research Society, Mar. 1998.
Murch, Kehr, "The Search for Low-Smoke Polyurethane Foams Goes on" Plastics Engineering, Jan. 1983, pp. 35-36.
Murray, "Total Knee Arthroplasty" Clinical Orthopaedics and Related Research, pp. 59-68.
N. Gvozdic and M. Dole, Crosslinking and Crystallinity in Irradiated Polyethylene, Papers presented at Anaheim meeting, vol. 19 (Mar. 1978).
Norman S. Allen, et al., Thermal and Photo-chemical Degradation of Nylon 6,6 Polymer: Part 1—Influence of Amine-Carboxyl End Group Balance on Luminescent Species, Polymer Degradation and Stability 0141-3910/87/$03-50© Elsevier Applied Science Publishers Ltd. England, 1987, pp. 77-95.
Nusbaum et al., "Wear Mechanisms for Ultrahigh Molecular Weight Polyethylene in the Total Hip Prosthesis" Journal of Applied Polymer Science, vol. 23, pp. 777-789, 1979.
O'Neill, Birkinshaw, Leahy and Barklie, "The role of long lived free radicals in the ageing of irradiated ultra high molecular weight polyethylene", Polymer Degradation and Stability 63 (1999), 31-39.
Office Action from corresponding Japanese Application JP 2003-161581.
Okada, Amemiya, "Effect of Atmosphere on Radiation-Induced Crosslinking of Polyethylene" Journal of Polymer Science, vol. L, Issue 153, pp. S22-S24, 1961.
Oonishi, H., Takayama, Y., and Tsuji, E. Improvement of Polyethylene by Irradiation in Artificial Joints, Radiat. Phys. Chem., vol. 39, No. 6, pp. 495-504, (1992).
Oppenheimer B, Oppenheimer T, Danishefsky, Stout and Eirich, "Further Studies of Polymers as Carcinogenic Agents in Animals", Cancer Research, pp. 333-340.
Orhun K. Muratoglu, et al., A Comparison of 5 Different Types of Highly Crosslinked Uhmwpes: Physical Properties and Wear Behavior, 1999 Society for Biomaterials, 25th Annual Meeting Transactions, pp. 326, 496, 782, 212 and 500.
Orhun K. Muratoglu, et al., Unified Wear Model for Highly Crosslinked Ultra-High Molecular Weight Polyethylenes (UHMWPE), Biomaterials (20) (1999), pp. 1463-1470.

SEQUENTIALLY CROSS-LINKED POLYETHYLENE

CROSS-REFERENCE TO RELATED APPLICATIONS

This application is a continuation of U.S. application Ser. No. 13/223,422, filed Sep. 1, 2011 now U.S. Pat. No. 8,324,291, which is a continuation of U.S. application Ser. No. 12/757,394, filed Apr. 9, 2010, now U.S. Pat. No. 8,030,370, which is a continuation of U.S. application Ser. No. 12/315,994, filed Dec. 9, 2008, now U.S. Pat. No. 7,714,036, which is a continuation of U.S. application Ser. No. 10/957,782, filed Oct. 4, 2004, now U.S. Pat. No. 7,517,919, which is a continuation of U.S. application Ser. No. 10/454,815, filed Jun. 4, 2003, now abandoned, which claimed the benefit of the filing date of U.S. Provisional Patent Application No. 60/386,660 filed Jun. 6, 2002, the disclosures of which are hereby incorporated herein by reference.

BACKGROUND OF THE INVENTION

This invention relates to medical implants formed of a polymeric material such as ultra-high molecular weight polyethylene, with superior oxidation and wear resistance produced by a sequential irradiation and annealing process.

Various polymer systems have been used for the preparation of artificial prostheses for biomedical use, particularly orthopedic applications. Among them, ultra-high molecular weight polyethylene is widely used for articulation surfaces in artificial knee, hip, and other joint replacements. Ultra-high molecular weight polyethylene (UHMWPE) has been defined as those linear polyethylenes which have a relative viscosity of 2.3 or greater at a solution concentration of 0.05% at 135° C. in decahydronaphthalene. The nominal weight-average molecular weight is at least 400,000 and up to 10,000,000 and usually from three to six million. The manufacturing process begins with the polymer being supplied as fine powder which is consolidated into various forms, such as rods and slabs, using ram extrusion or compression molding. Afterwards, the consolidated rods or slabs are machined into the final shape of the orthopedic implant components. Alternatively, the component can be produced by compression molding of the UHMWPE resin powder.

All components must then go through a sterilization procedure prior to use, but usually after being packaged. There exists several sterilization methods which can be utilized for medical applications, such as the use of ethylene oxide, gas plasma, heat, or radiation. However, applying heat to a packaged polymeric medical product can destroy either the integrity of the packaging material (particularly the seal, which prevents bacteria from going into the package after the sterilization step) or the product itself.

It has been recognized that regardless of the radiation type, the high energy beam causes generation of free radicals in polymers during radiation. It has also been recognized that the amount or number of free radicals generated is dependent upon the radiation dose received by the polymers and that the distribution of free radicals in the polymeric implant depends upon the geometry of the component, the type of polymer, the dose rate, and the type of radiation beam. The generation of free radicals can be described by the following reaction (which uses polyolefin and gamma ray irradiation for illustration):

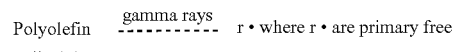

(1)

* (through C-C chain scission or C-H scission)

Depending on whether or not oxygen is present, primary free radicals r. will react with oxygen and the polymer according to the following reactions as described in "Radiation Effects on Polymers," edited by Roger L. Clough and Shalaby W. Shalaby, published by American Chemical Society, Washington, D.C., 1991.

In the Presence of Oxygen

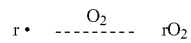

(2)

(3)

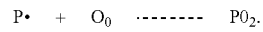

(4)

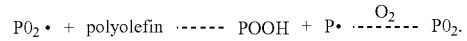

(5)

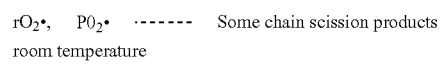

(6)

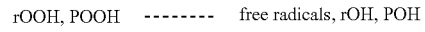

(7)

(8)

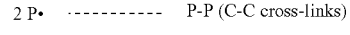

(9)

In radiation in air, primary free radicals r. will react with oxygen to form peroxyl free radicals $rO_2.$, which then react with polyolefin (such as UHMWPE) to start the oxidative chain scission reactions (reactions 2 through 6). Through these reactions, material properties of the plastic, such as molecular weight, tensile and wear properties, are degraded.

It has been found that the hydroperoxides (rOOH and POOH) formed in reactions 3 and 5 will slowly break down as shown in reaction 7 to initiate post-radiation degradation. Reactions 8 and 9 represent termination steps of free radicals to form ester or carbon-carbon cross-links. Depending on the type of polymer, the extent of reactions 8 and 9 in relation to reactions 2 through 7 may vary. For irradiated UHMWPE, a value of 0.3 for the ratio of chain scission to cross-linking has been obtained, indicating that even though cross-linking is a dominant mechanism, a significant amount of chain scission occurs in irradiated polyethylene.

By applying radiation in an inert atmosphere, since there is no oxidant present, the primary free radicals r. or secondary free radicals P. can only react with other neighboring free radicals to form carbon-carbon cross-links, according to reactions 10 through 12 below. If all the free radicals react through reactions 10 through 12, there will be no chain scission and there will be no molecular weight degradation. Furthermore, the extent of cross-linking is increased over the original polymer prior to irradiation. On the other hand, if not all the free radicals formed are combined through reactions 10, 11 and 12, then some free radicals will remain in the plastic component.

In an Inert Atmosphere

$r. + \text{polyolefin} \text{---} P.$  (10)

$2r. \text{----} r\text{-}r (\text{C—C cross-linking})$  (11)

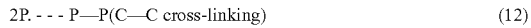

$2P. \text{----} P\text{—}P (\text{C—C cross-linking})$  (12)

It is recognized that the fewer the free radicals, the better the polymer retains its physical properties over time. The greater the number of free radicals, the greater the degree of molecular weight and polymer property degradation will occur. Applicant has discovered that the extent of completion of free radical cross-linking reactions is dependent on the reaction rates and the time period given for reaction to occur.

UHMWPE is commonly used to make prosthetic joints such as artificial hip joints. In recent years, it has been found that tissue necrosis and interface osteolysis may occur in response to UHMWPE wear debris. For example, wear of acetabular cups of UHMWPE in artificial hip joints may introduce microscopic wear particles into the surrounding tissues.

Improving the wear resistance of the UHMWPE socket and, thereby, reducing the rate of production of wear debris may extend the useful life of artificial joints and permit them to be used successfully in younger patients. Consequently, numerous modifications in physical properties of UHMWPE have been proposed to improve its wear resistance.

It is known in the art that ultrahigh molecular weight polyethylene (UHMWPE) can be cross-linked by irradiation with high energy radiation, for example gamma radiation, in an inert atmosphere or vacuum. Exposure of UHMWPE to gamma irradiation induces a number of free-radical reactions in the polymer. One of these is cross-linking. This cross-linking creates a 3-dimensional network in the polymer which renders it more resistant to adhesive wear in multiple directions. The free radicals formed upon irradiation of UHMWPE can also participate in oxidation which reduces the molecular weight of the polymer via chain scission, leading to degradation of physical properties, embrittlement and a significant increase in wear rate. The free radicals are very long-lived (greater than eight years), so that oxidation continues over a very long period of time resulting in an increase in the wear rate as a result of oxidation over the life of the implant.

Sun et al. U.S. Pat. No. 5,414,049, the teachings of which are incorporated herein by reference, broadly discloses the use of radiation to form free radicals and heat to form cross-links between the free radicals prior to oxidation.

Hyon et al. U.S. Pat. No. 6,168,626 relates to a process for forming oriented UHMWPE materials for use in artificial joints by irradiating with low doses of high-energy radiation in an inert gas or vacuum to cross-link the material to a low degree, heating the irradiated material to a temperature at which compressive deformation is possible, preferably to a temperature near the melting point or higher, and performing compressive deformation followed by cooling and solidifying the material. The oriented UHMWPE materials have improved wear resistance. Medical implants may be machined from the oriented materials or molded directly during the compressive deformation step. The anisotropic nature of the oriented materials may render them susceptible to deformation after machining into implants.

Salovey et al. U.S. Pat. No. 6,228,900, the teachings of which are incorporated by reference, relates to a method for enhancing the wear-resistance of polymers, including UHMWPE, by cross-linking them via irradiation in the melt.

Saum et al. U.S. Pat. No. 6,316,158 relates to a process for treating UHMWPE using irradiation followed by thermally treating the polyethylene at a temperature greater than 150° C. to recombine cross-links and eliminate free radicals.

Several other prior art patents attempt to provide methods which enhance UHMWPE physical properties. European Patent Application 0 177 522 81 relates to UHMWPE powders being heated and compressed into a homogeneously melted crystallized morphology with no grain memory of the UHMWPE powder particles and with enhanced modulus and strength. U.S. Pat. No. 5,037,928 relates to a prescribed heating and cooling process for preparing a UHMWPE exhibiting a combination of properties including a creep resistance of less than 1% (under exposure to a temperature of 23° C. and a relative humidity of 50% for 24 hours under a compression of 1000 psi) without sacrificing tensile and flexural properties. U.K. Patent Application GB 2 180 815 A relates to a packaging method where a medical device which is sealed in a sterile bag, after radiation/sterilization, is hermetically sealed in a wrapping member of oxygen-impermeable material together with a deoxidizing agent for prevention of post-irradiation oxidation.

U.S. Pat. No. 5,153,039 relates to a high density polyethylene article with oxygen barrier properties. U.S. Pat. No. 5,160,464 relates to a vacuum polymer irradiation process.

BRIEF SUMMARY OF THE INVENTION

The present invention relates to a method for providing a polymeric material, such as UHMWPE, with superior oxidation resistance, mechanical strength and wear properties. For the purpose of illustration, UHMWPE will be used as an example to describe the invention. However, all the theories and processes described hereafter should also apply to other polymeric materials such as polypropylene, high density polyethylene, polyhydrocarbons, polyester, nylon, polyurethane, polycarbonates and poly(methylmethcrylate) unless otherwise stated. The method involves using a series of relatively low doses of radiation with an annealing process after each dose.

As stated above, UHMWPE polymer is very stable and has very good resistance to aggressive media except for strong oxidizing acids. Upon irradiation, free radicals are formed which cause UHMWPE to become activated for chemical reactions and physical changes. Possible chemical reactions include reacting with oxygen, water, body fluids, and other chemical compounds while physical changes include density, crystallinity, color, and other physical properties. In the present invention, the sequential radiation and annealing process greatly improves the physical properties of UHMWPE when compared to applying the same total radiation dose in one step. Furthermore, this process does not employ stabilizers, antioxidants, or any other chemical compounds which may have potentially adverse effects in biomedical or orthopedic applications.

It is also known that at relatively low dose levels (<5 MRads) of irradiation residual free radicals are mostly trapped in the crystalline region while most free radicals crosslink in the amorphous region. There is a steep free radical concentration gradient across the crystalline-amorphous boundary, which provides a significant driving force for free radicals to diffuse into the amorphous region where they can crosslink upon subsequent annealing. However, if the polyethylene is allowed to continuously accumulate higher radiation doses without interruptive annealing, molecules in the amorphous region become more and more stiffened due to increased crosslinking. As a result, the amorphous region traps more and more free radicals. This leads to a diminished free radical gradient across the crystalline-amorphous boundary, thereby reducing the driving force for free radical diffusion upon subsequent annealing. By limiting the incremental dose to below 5 MRads and preferably below 3.5 MRads and following with annealing, a relatively higher free radical diffusion driving force can be maintained, allowing a more efficient free radical reduction upon annealing. If higher radiation doses are used, there could be cross-linking at the chain folded crystal surfaces. This could hamper the movement of free radicals from the crystal to the amorphous regions.

It has been found that polyethylene crystallinity increases continuously with increasing radiation-doses due to chain-scission (approximately 55% before radiation, increasing to 60% at 3.0 MRads, and to 65% at 10 MRads).

As the crystallinity increases with increasing dose of radiation, more residual free radicals are created and stored in the extra crystalline regions, which makes it increasingly more difficult to eliminate free radicals by annealing below the melt temperature. However, treating above the melting temperature (re-melting) significantly alters the crystallinity and crystal morphology which leads to significant reduction in mechanical properties such as yield strength and ultimate tensile strength and creep resistance and these properties are important for the structural integrity of the implant.

An orthopedic preformed material such as a rod, bar or compression molded sheet for the subsequent production of a medical implant such as an acetabular or tibial implant with improved wear resistance is made from a polyethylene material cross-linked at least twice by irradiation and thermally treated by annealing after each irradiation. The material is cross-linked by a total radiation dose of from about 2 MRads to 100 MRads and preferably between 5 MRads and 10 MRads. The incremental dose for each irradiation is between about 2 MRads and about 5 MRads. The weight average molecular weight of the material is over 400,000.

The annealing takes place at a temperature greater than 25° C., preferably between 110° C. and 135° C. but less than the melting point. Generally, the annealing takes place for a time and temperature selected to be at least equivalent to heating the irradiated material at 50° C. for 144 hours as defined by Arrenhius' equation 14. The material is heated for at least about 4 hours and then cooled to room temperature for the subsequent irradiation in the series.

By limiting the incremental dose to below 5 MRads and preferably below 3.5 MRads and following with annealing, the crystallinity will fluctuate between 55% and 60% (instead of 55-65%) and hence both the amount of chain-scission and residual free-radical concentration can be significantly reduced.

The polyethylene of the present invention may be in the form of a preformed rod or sheet with a subsequent production of a medical implant with improved wear resistance. The preformed rod or sheet is cross-linked at least twice by irradiation and thermally treated by annealing after each radiation. The incremental dose for each radiation is preferably between about 2 and 5 MRads with the total dose between 2 and 100 MRads and preferably between 5 and 10 MRads.

After each irradiation, the preformed material is annealed either in air or in an inner atmosphere at a temperature of greater than 25° C. and preferably less than 135° C. or the melting point. Preferably, the annealing takes place for a time and temperature selected to be at least equivalent to heating the irradiated material at 50° C. for 144 hours as defined by Arrenhius' equation (14). Generally, each heat treatment lasts for at least 4 hours and preferably about 8 hours.

The preformed polyethylene material is then machined into a medical implant or other device. If the irradiation process occurred in air, then the entire outer skin to about 2 mm deep is removed from the preform prior to machining the medical implant or other device. If the process was done in a vacuum or an inner atmosphere such a nitrogen, then the outer skin may be retained.

The end-results of reduced chain-scission and free-radical concentration are improved mechanical properties, improved oxidation resistance and enhanced wear resistance.

DETAILED DESCRIPTION

Figure 1:
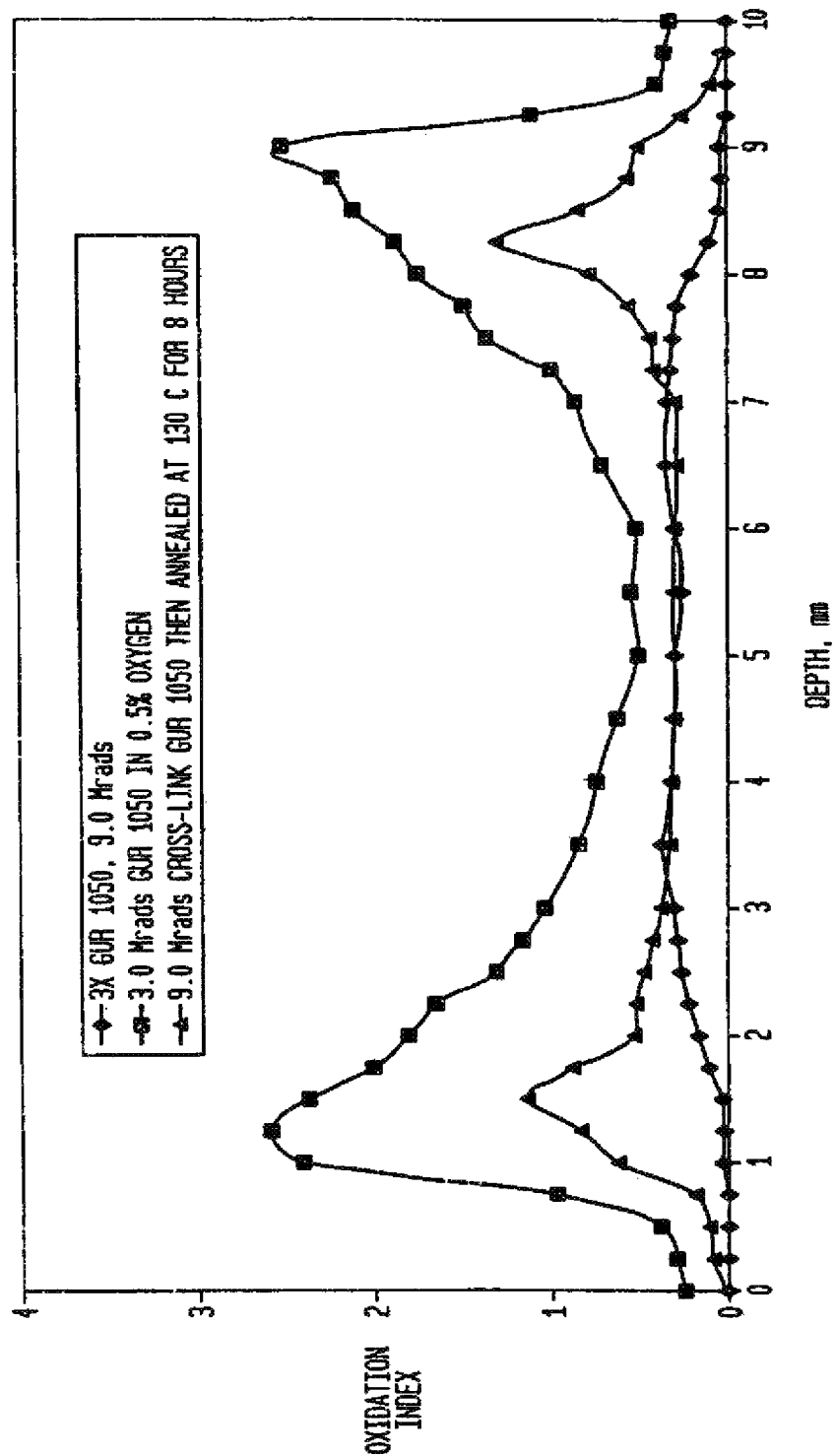
FIG. 1 shows the oxidation index profiles of the specimens of Example 8.

Abbreviations used in this application are as follows:
UHMW—ultra-high molecular weight
UHMWPE—ultra-high molecular weight polyethylene
HMW—high molecular weight
HMWPE—high molecular weight polyethylene This invention provides a method for improving the wear resistance of a polymer by crosslinking (preferably the bearing surface of the polymer) and then thermally treating the resulting polymer. Preferably, the most oxidized surface of the polymer is also removed. Also presented are the methods for using the polymeric compositions for making products and the resulting products, e.g., in vivo implants.

The method of the invention utilizes at least two separate irradiations for crosslinking a polymer followed by a like number of thermal treatments to decrease the free radicals to produce either a treated fully formed or a preformed polymeric composition. The term "preformed polymeric composition" means that the polymeric composition is not in a final desired shape or from (i.e., not a final product). For example, where the final product of the preformed polymeric composition is an acetabular cup, the at least two irradiations and thermal treatments of the polymer could be performed at pre-acetabular cup shape, such as when the preformed polymeric composition is in the form of a solid bar or block. Of course, the process of the present invention could be applied to a fully formed implant if the process is done with the implant in an oxygen reduced atmosphere.

In the present invention, the wear resistance of a polymer is improved by crosslinking. The crosslinking can be achieved by various methods known in the art, for example, by irradiation from a gamma radiation source or from an electron beam, or by photocrosslinking. The preferred method for crosslinking the polymer is by gamma irradiation. The polymer is preferably crosslinked in the form of an extruded bar or molded block.

In the preferred method, the crosslinked polymer is subjected to thermal treatment such as by annealing (i.e. heated above at or below the melting temperature of the crosslinked polymer) to produce the preformed polymeric composition.

In the preferred embodiment of the invention, the outer layer of the resulting preformed polymeric composition, which is generally the most oxidized and least crosslinked and, thus, least wear resistant, is removed. For example, the bearing surface of the preformed polymeric composition may be fashioned from inside, e.g., by machining away the surface of the irradiated and thermally treated composition before or during fashioning into the final product, e.g., into an implant. Bearing surfaces are surfaces which are in moving contact, e.g., in a sliding, pivoting, or rotating relationship to one another.

High molecular weight (HMW) and ultra-high molecular weight (UHMW) polymers are preferred, such as HMW polyethylene (HMWPE), UHMW polyethylene (UHMWPE), and UHMW polypropylene. HMW polymers have molecular weights ranging from about $10^5$ grams per mole to just below $10^6$. UHMW polymers have molecular weights equal to or higher than $10^6$ grams per mole, preferably from $10^6$ to about $10^7$. The polymers are generally between about 400,000 grams per mole to about 10,000,000 and are preferably polyolefinic materials.

For implants, the preferred polymers are those that are wear resistant and have exceptional chemical resistance. UHMWPE is the most preferred polymer as it is known for these properties and is currently widely used to make acetabular cups for total hip prostheses and components of other joint replacements. Examples of UHMWPE are those having molecular weight ranging from about 1 to $8\times10^6$ grams per mole, examples of which are: GUR 1150 or 1050 (Hoechst-Celanese Corporation, League City, Tex.) with a weight average molecular weight of 5 to $6\times10^6$ grams per mole; GUR 1130 with a weight average molecular weight of 3 to $4\times10^6$; GUR 1120 or 1020 with a weight average molecular weight of 3 to $4\times10^6$; RCH 1000 (Hoechst-Celanese Corp.) with a weight average of molecular weight of $4\times10^6$ and HiFax 1900 of 2 to $4\times10^6$ (HiMont, Elkton, Md.). Historically, companies which make implants have used polyethylenes such as HIFAX 1900, GUR 1020, GUR 1050, GUR 1120 and GUR 1150 for making acetabular cups.

Sterilization Methods: All polymeric products must be sterilized by a suitable method prior to implanting in the human body. For the formed crosslinked and thermally treated polymeric compositions (i.e., the final products) of the present invention, it is preferable that the products be sterilized by a non-radiation based method, such as ethylene oxide or gas plasma, in order not to induce additional crosslinking free radicals and/or oxidation of the previously treated preformed polymeric composition. Compared to radiation sterilization, a non-radiation sterilization method has a minor effect on the other important physical characteristics of the product.

The degree of crystallinity can be determined using methods known in the art, e.g. by differential scanning calorimetry (DSC), which is generally used to assess the crystallinity and melting behavior of a polymer. Wang, X. & Salovey, R., *J. App. Polymer Sci.*, 34:593-599 (1987).

Wide-angle X-ray scattering from the resulting polymer can also be used to further confirm the degree of crystallinity of the polymer, e.g. as described in Spruiell, J. E., & Clark, E. S., in "*Methods of Experimental-Physics*," L. Marton & C. Marton, Eds., Vol. 16, Part B, Academic Press, New York (1980). Other methods for determining the degree of crystallinity of the resulting polymer may include Fourier Transform Infrared Spectroscopy (FTIR), e.g., as described in "Fourier Transform Infrared Spectroscopy And Its Application To Polymeric Materials," John Wiley and Sons, New York, U.S.A. (1982)} and density measurement (ASTM D1505-68). Measurements of the gel content and swelling are generally used to characterize crosslink distributions in polymers; the procedure is described in Ding, Z. Y., et al., *J. Polymer Sci., Polymer Chem.*, 29:1035-38 (1990). FTIR can also be used to assess the depth profiles of oxidation as well as other chemical changes such as unsaturation {Nagy, E. V. & Li, S., "A Fourier transform infrared technique for the evaluation of polyethylene orthopedic bearing materials," *Trans. Soc. for Biomaterials*, 13:109 (1990); Shinde, A. & Salovey, R., *J. Polymer Sci., Polm. Phys. Ed.*, 23:1681-1689 (1985)}.

Another aspect of the invention presents a process for making implants using the preformed polymeric composition of the present invention. The preformed polymeric composition may be shaped, e.g., machined, into the appropriate implants using methods known in the art. Preferably, the shaping process, such as machining, removing the oxidized surface of the composition.

The preformed polymeric compositions of the present invention can be used in any situation where a polymer, especially UHMWPE, is called for, but especially in situations where high wear resistance is desired. More particularly, these preformed polymeric compositions are useful for making implants.

An important aspect of this invention presents implants that are made with the above preformed polymeric compositions or according to the methods presented herein. In particular, the implants are produced from preformed polymeric composition made of UHMWPE irradiated and crosslinked at least twice each time followed by annealing and then removing the oxidized surface layer and then fabricating into a final shape. The preformed polymeric composition of the present invention can be used to make the acetabular cup, or the insert or liner of the cup, or trunnion bearings (e.g. between the modular head and the hip stem). In the knee joint, the tibial plateau (femoro-tibial articulation), the patellar button (patello-femoral articulation), and/or other bearing components, depending on the design of the artificial knee joint. These would include application to mobile bearing knees where articulation between the tibial insert and tibial tray occurs. In the shoulder, the process can be used in the glenoid component. In the ankle joint, the preformed polymeric composition can be used to make the talar surface (tibiotalar articulation) and other bearing components. In the elbow joint, the preformed polymeric composition can be used to make the radio-humeral joint, ulno-humeral joint, and other bearing components. In the spine, the preformed polymeric composition can be used to make intervertebral disk replacement and facet joint replacement. The preformed polymeric composition can also be made into temporo-mandibular joint (jaw) and finger joints. The above are by way of example, and are not meant to be limiting.

The following discusses the first and second aspects of the invention in more detail.

First Aspect of the Invention: Polymeric Compositions with Increased Wear Resistance.

The first aspect of the invention provides preformed polymeric compositions which are wear resistant and useful for making in vivo implants. In this aspect, for polymers in general, and more preferably UHMW and HMW polymers, and most preferably UHMWPE and HMWPE, the at least two (2) incremental irradiation doses are preferably from about 1 to about 100 Mrad, and more preferably, from about 2 to about 5 Mrad. This most preferable range is based on achieving a reasonable balance between improved wear resistance and minimal degradation of other important physical properties. The total dose is between 2 and 100 MRad and more preferably 5 to about 10 MRads.

In vivo implants of the present invention, i.e., irradiated within the above dose ranges are expected to function in vivo without mechanical failure. The UHMWPE acetabular cups used by Oonishi et al. [in *Radiat. Phys. Chem.*, 39:495-504 (1992)] were irradiated to 100 Mrad and functioned in vivo without reported mechanical failure as long as 26 years of clinical use. Furthermore, it is surprising that, as shown in the EXAMPLES, acetabular cups from the preformed polymeric composition prepared according to the present invention, but irradiated to much less than 100 Mrad, exhibited much higher wear resistance than reported by Oonishi et al.

On the other hand, if a user is primarily concerned with reducing wear, and other physical properties are of secondary concern, then a higher dose than the above stipulated most preferable range (e.g., 5 to 10 Mrad) may be appropriate, or vice versa (as illustrated in the detailed examples in the following section). The optimum radiation dose is preferably based on the total dose received at the level of the bearing surface in the final product. Gamma radiation is preferred.

The preferred annealing temperature after each sequential irradiation is below the melting temperature of the UHMWPE which is generally below 135° C.

The annealing temperature is preferably from about room temperature to below the melting temperature of the irradiated polymer; more preferably from about 90° C. to about 1° C. below the melting temperature of the irradiated polymer; and most preferably from about 110° C. to about 130° C. For example, UHMWPE may be annealed at a temperature from about 25° C. to about 140° C., preferably from about 50° C. to about 135° C. and more preferably from about 80° C. to about 135° C. and most preferably between 110° C. to 130° C. The annealing period is preferably from about 2 hours to about 7 days, and more preferably from about 7 hours to about 5 days and most preferably from about 10 hours to about 24 hours.

Instead of using the above range of radiation dose as a criterion, the appropriate amount of crosslinking may be determined based on the degree of swelling, gel content, or molecular weight between crosslinks after thermal treatment. This alternative is based on the applicant's findings (detailed below) that acetabular cups made from UHMWPE falling within a preferred range of these physical parameters have reduced or non-detectable wear. The ranges of these physical parameters include one or more of the following: a degree of swelling of between about 1.7 to about 5.3; molecular weight between crosslinks of between about 400 to about 8400 g/mol; and a gel content of between about 95% to about 99%. A preferred polymer or final product has one or more, and preferably all, of the above characteristics. These parameters can also be used as starting points in the second aspect of the invention (as illustrated by the flowchart, discussed below) for determining the desired radiation dose to balance the improvement in wear resistance with other desired physical or chemical properties, such as polymer strength or stiffness.

After crosslinking and thermal treatment, preferably, the most oxidized surface of the preformed polymeric composition is removed. The depth profiles of oxidation of the preformed polymeric composition can be determined by methods known in the art, such as FTIR. In general, the most oxidized surface of preformed polymeric composition which is exposed to air is removed, e.g. by machining, before or while fashioning the preformed polymeric composition into the final product. Since oxygen diffuses through the polyethylene with time, the sequential irradiation/annealing preferably should be completed prior to oxygen diffusing in high concentrations to the area of the preform from which the final part is made.

As noted above, the most preferable range of total dose for crosslinking radiation (i.e., from 5 to 10 Mrad) was based on Wang et al. "Tribology International" Vol. 3, No. 123 (1998) pp. 17-35. After irradiation in air the gap in time before annealing is preferably seven days but at least before any oxygen diffuses into the area of the rod from which the implant is made. It has been found that it takes at least seven days to diffuse through the surface layer.

Free radicals generated during an irradiation step should be reduced to an acceptable level by annealing before exposure to oxygen. The portion of the material from which the implant is made contains free radicals and if it is exposed to air or other oxidants after the manufacturing process, oxidation will occur. The bulk portion of the polymer from which the implant is to be made should be annealed at an elevated temperature while out of contact with oxygen for a prescribed time. This is because the rate of free radical reactions (reactions 10 through 12) increases with increasing temperature, according to the following general expressions:

$$\frac{dr\cdot}{dt} = k_1[r\cdot] \text{ and } \frac{dP\cdot}{dt} = k_2[P\cdot] \tag{13}$$

Compared to room temperature, an elevated temperature not only increases the reaction rate constants, $k_1$ and $k_2$, but also helps free radicals r. and P. to migrate in the plastic matrix to meet other neighboring free radicals for cross-linking reactions. In general, the desired elevated temperature is between room temperature to below the melting point of the polymer. For UHMWPE, this temperature range is between about 25° C. and about 140° C. It is to be noted that the higher the temperature used, the shorter the time period needed to combine free radicals. Additionally, due to the high viscosity of a UHMWPE melt, the formed UHMWPE often contains residual (internal) stress caused by incomplete relaxation during the cooling process, which is the last step of the forming process. The annealing process described herein will also help to eliminate or reduce the residual stress. A residual stress contained in a plastic matrix can cause dimensional instability and is in general undesirable.

In the preferred embodiment, the sequential irradiation followed by sequential annealing after each irradiation is preformed in air on a preform such as an extruded rod, bar or compression molded sheet made from polyethylene and preferably UHMWPE. Obviously, the final sequential annealing must take place prior to the bulk material of the final part or implant being exposed to air. Normally, it takes at least seven days for atmospheric oxygen to diffuse through the outer layer of polyethylene and deeply enough into rod, bar or sheet to effect the bulk polyethylene forming the final part. Therefore, the last annealing in the sequence preferably should take place prior to the time required for the oxygen to diffuse deeply into the rod. Of course, the more material which must be machined off to reach the finished part, the longer one can wait for the completion of the sequential irradiation and annealing process.

If the sequential irradiation/annealing process is performed on a final product, such as an acetabular cup, after machining, the polymeric component is preferably packaged in an air tight package in an oxidant-free atmosphere, i.e. less than 1% volume by volume. Thus, all air and moisture must be removed from the package prior to the sealing step. Machines to accomplish this are commercially available, such as from Orics Industries Inc., College Point, New York, which flush the package with a chosen inert gas, vacuum the container, flush the container for the second time, and then heat seal the container with a lid. In general, less than 0.5% (volume by volume) oxygen concentration can be obtained consistently. An example of a suitable oxidant impermeable (air tight) packaging material is polyethylene terephthalate (PET). Other examples of oxidant impermeable packaging material is poly(ethylene vinyl alcohol) and aluminum foil, whose oxygen and water vapor transmission rates are essentially zero. All these materials are commercially available. Several other suitable commercial packaging materials utilize a layer structure to form a composite material with superior oxygen and moisture barrier properties. An example of this type is a layered composite comprised of polypropylene/poly (ethylene vinyl alcohol)/polypropylene.

With a final product, following each irradiation step, the heat treatment or annealing step should be performed while the implant is out of contact with oxygen or in an inert atmosphere and at an elevated temperature to cause free radicals to form cross-links without oxidation. If proper packaging materials and processes are used and oxidant transmission rates are minimal, then the oxidant-free atmosphere can be maintained in the package and a regular oven with air circulation can be used for heat treatment after sterilization. To absolutely ensure that no oxidants leak into the package, the oven may be operated under a vacuum or purged with an inert gas. In general, if a higher temperature is used, a shorter time period is required to achieve a prescribed level of oxidation resistance and cross-linking. In many cases, the relationship between the reaction temperature and the reaction rate follows the well-known Arrhennius equation:

$$k_1 \text{ or } k_2 = A^*\exp(-\Delta H/RT) \quad (14)$$

where $k_1$ and $k_2$ are reaction rate constants from reactions 13 and 14
A is a reaction dependent constant
$\Delta H$ is activation energy of reaction
T is absolute temperature (K)
R is the universal gas constant.

It is very important to ensure that the number of free radicals has been reduced to a minimal or an accepted level by the heat treatment. This is because the presence of an oxidant causes not only the oxidation of pre-existing free radicals, but also the formation of new free radicals via reactions 2 through 7. When the number of free radicals grows, the extent of oxidation and the oxidation rate will increase according to the following equations:

$$\frac{dr\cdot}{dt} = k_3[r\cdot][O_2] \text{ and } \frac{dP\cdot}{dt} = k_4[P\cdot][O_2] \quad (15)$$

Where free radicals r. and P. can grow in number in the presence of oxidants and in turn increase the oxidation rates. It is also to be noted that the oxidation reaction rate constants $k_3$ and $k_4$ increase with increasing temperature, similar to $k_1$ and $k_2$. Therefore, to determine if a certain level of residual free radicals is acceptable or not, it is required to evaluate specific material properties after the plastic sample is stored or aged at the application temperature for a time period which is equal to or longer than the time period intended for the application of the plastic component. An alternative to the method to assess the aging effect is to raise the aging temperature of the plastic sample for a shorter time period. This will increase the reaction rate constants $k_3$ and $k_4$ significantly and shorten the aging time. It has been found that an acceptable level of residual free radicals is $1.0 \times 10^{17}/g$ for UHMWPE use for orthopedic implants.

Example I

As stated above, the ultra-high molecular weight polyethylene extruded rod is irradiated for a sufficient time for an accumulated incremental dose of between 2 and 5 (MRads) (20 to 50 kGy). After this irradiation step, the extruded rod is annealed in air preferably at a temperature below its melting point, preferably at less than 135° C. and more preferably between 110° C. and 130° C. The irradiation and annealing steps are then repeated two or more times so that the total radiation dose is between 4 and 15 MRads (50 to 150 kGy). In this example, the rod is irradiated for a total dose of 3 MRad and then annealed at 130° C. for 24 hours, allowed to cool to room temperature and sit for 3 days and then reirradiated for a dose of 3.0 MRads (a total dose of 6 MRads) again annealed at 130° C. for 24 hours, allowed to cool at room temperature and sit for an additional 3 days and then irradiated a third time with a 3.0 MRad dose (for a total of 9 MRads) and again annealed at 130° C. for 24 hours. The rod is cooled to room temperature and is then moved into the manufacturing process which forms the orthopedic implant by machining.

The above example can also be applied to compression molded sheet with, for example, a tibial component being manufactured out of the sequentially irradiated and annealed material.

In the preferred embodiment, the total radiation dose can be anywhere between 5 and 15 MRads and most preferably 9 MRads applied in three doses of 3 MRads, as done in the above example. The length of time between sequential irradiation is preferably between 3 to 7 days. While the annealing step is preferably performed after the irradiation step, it is possible to heat the rod to the annealing temperatures and irradiate it sequentially in the heated state. The rod may be allowed to cool between doses or can be maintained at the elevated temperatures for the entire series of doses.

Example II

A machined tibial implant in its final form is packaged in an oxygen reduced atmosphere having an oxygen concentration less than 1% volume by volume. The packaged implant is then processed as described in Example I through a series of three (3) irradiation and annealing cycles as described above with the total radiation dose being 9 MRads. The implant was then boxed and ready for final shipping and use.

Example III

Two ultra-high molecular weight polyethylene rods (one of compression molded GUR 1020 and the other of ram extruded GUR 1050) with a cross-section profile of 2.5-inch× 3.5-inch (GUR 1020) and 3.5-inch diameter (GUR 1050), respectively, were used. Lengths of these rods were sectioned into 18-inch lengths; three 18-inch rods (staggered and separated by small paper boxes) were packaged in a paper carton before the sequential radiation process. The purpose of the packaging and staggering was to reduce the possibility of blocking the radiation (gamma rays) to each individual rod during the process.

The rods went through the following sequential process in air:
1. Each rod received a nominal dose of 30 kGy gamma radiation;
2. Each was then annealed at 130° C. for 8 hours; and
3. Steps 1 and 2 were repeated two more times. Preferably, the repeated steps occurred within three days each.

While the process was done in air, it could be performed in an inert atmosphere such as nitrogen.

The rods received a nominal 90 kGy total dosage of gamma radiation after the completion of the above sequential process. The GUR 1020 rod is designated as sample "A" and the GUR 1050 rod as sample "B". When done in air, 2 mm of the entire outer surface of each rod is removed after the entire process is complete.

Control

The following materials/process had been selected as "Control":

1. The conventionally (in nitrogen or vacuum $N_2VAC$) processed molded GUR 1020 and extruded GUR 1050 rods received in a single dose 30 kGy gamma radiation sterilization in nitrogen but no annealing and were designated samples "C" and "D," respectively.

2. A GUR 1050 rod that received 90 kGy total dose (non-sequentially) followed by annealing at 130° C. for 8 hours and was designated as sample "E".

Tensile Test

The ASTM D 638 Type IV specimens were used for the tensile property evaluation of samples A-E. Tensile properties were determined from the average of six (6) specimens. An Instron Model 4505 Test System was used to conduct this evaluation. Crosshead speed was 5.0 mm/min. The results are listed in Table I.

Free Radical Concentration Measurement

All free radical measurement was conducted before the accelerated aging treatment. The specimens are 3 mm diameter, 10 mm long cylinders. This evaluation was carried out at the University of Memphis (Physics Department). Free radical concentration was measured and calculated from average of three (3) specimens. Free radical measurements were performed using electron spin resonance technique. This is the only technique that can directly detect free radicals in solid and aqueous media. An ESR spectrometer (Bruker EMX) was used in this evaluation.

Oxidation Resistance Measurement

Oxidation index/profile measurement was performed after accelerated aging using the protocol per ASTM F 2003 (5 atm O2 pressure at 70° C. for 14 days) on specimens machined into 90×20×10 mm thick rectangular blocks from the center of the rods. The oxidation analysis was performed on a Nicolet model 750 Magna-IR™ spectrometer per ASTM F2102-01 using an aperture 100 μm×100 μm and 256 scans. An oxidation index was defined by the ratio of the carbonyl peak area (1660 to 1790 cm$^{-1}$) to the 1370 cm$^{-1}$ peak area (1330 to 1390 cm$^{-1}$). A through-the-thickness (10 mm) oxidation index profile is generated from an average of three (3) specimens. The 0 and 10 mm depths represent upper and lower surfaces of specimens. The maximum oxidation index of each specimen was used to determine if there was a significant difference.

Statistical Analysis—Student's t Test—Test of Significance

A student's t test (two-tail, unpaired) was conducted to measure statistical significance at the 95% confidence level ($p<0.05$).

Tensile Test Results

TABLE 1

Comparison Of Tensile Properties, N = 6

| Sample | Material | Yield Strength (MPa) | Ultimate Strength (MPa) | Elongation at Break (%) |
|---|---|---|---|---|
| A | GUR 1020 | 24.9 ± 0.6 | 59.3 ± 1.5 | 301 ± 7 |
| B | GUR 1050 | 25.6 ± 0.4 | 54.8 ± 1.2 | 255 ± 7 |
| C | GUR 1020 | 25.2 ± 0.1 | 57.0 ± 2.3 | 372 ± 10 |
| D | GUR 1050 | 24.5 ± 0.2 | 56.4 ± 4.0 | 370 ± 10 |
| E | GUR 1050 | 23.9 ± 0.4 | 51.0 ± 2.1 | 214 ± 5 |

The sequential process of samples "A" and "B" maintains both tensile yield and ultimate strength (when compared to their respective counterparts samples C and D). Consequently, the null hypothesis that sequential process maintains ($p=0.001$) tensile strengths was verified. Results also indicated that a sequential process improved elongation at break in radiation-crosslinked GUR 1050 by 19% ($p=0.001$) over a process that produced crosslinking by a single-dose delivery of 90 kGy (non-sequentially) and annealed at 130° C. for 8 hours (sample E).

The sequential crosslinking reduces free radical concentration in radiation-crosslinked GUR 1020 and 1050 by 87% ($p=0.001$) and 94% ($p=0.001$), respectively when comparing to their respective N2VAC™ process counterparts, samples C and D. The sequential crosslinking process also reduces free radical concentration in radiation-crosslinked GUR 1050 by 82% ($p=0.001$) over a process that produced crosslinking by a single-dose delivery of 90 kGy (non-sequentially) and annealed at 130° C. for 8 hours (sample E).

The sequential crosslinking process reduces the maximum oxidation index in radiation crosslinked GUR 1020 and 1050 by 82% ($p=0.001$) and 86% ($p=0.001$), respectively (when compared to control samples C and D). The process also reduces the maximum oxidation index in radiation-crosslinked GUR 1050 by 74% ($p=0.001$) over a process that produced crosslinking by a single-dose delivery of 90 kGy (non-sequentially) and annealed at 130° C. for at least 8 hours (sample E). The sequential irradiation and annealing process maintains the original tensile yield and ultimate strengths reduces free radical concentration and improves oxidation resistance. It is believed that sequential cross-linking is a gentler process than a single dose process.

Furthermore, this process has significant benefits over a single-dose delivery of 90 kGy (non-sequentially) and annealed at 130° C. for 8 hours in at least three areas. First there is a lower free radical concentration, second a better oxidation resistance and third a better tensile elongation.

While the preferred process is three sequential applications of 30 kGy each followed by annealing at 130° C. for eight (8) hours, a two step process of 30 kGy to 45 kGy radiation applied twice, each followed by an annealing at about 130° C. for about 8 hours may be used.

If it is desired to have an additional sterilization step after the sequential irradiation and annealing of the ultra-high molecular weight polyethylene preformed part or packaged final part then the part may be sterilized via non-irradiative methods such as ethylene oxide or gas plasma and then packaged or repackaged and shipped in the standard manner.

Example IV

Effect of Sequential Cross-Link Dose on the Physical Properties of UHMWPE

Materials and Methods

Medical-grade UHMWPE extruded bars (GUR 1050, Perplas Medical), with a weight average molecular weight of $5 \times 10^6$ Daltons and a diameter of 83 mm were used for all subsequent treatments. The GUR 1050 bars had a total original length of 5 meters and were extruded from the same polymer and extrusion lots. These bars were cut into 460 mm long sections and irradiated with gamma ray at room temperature in ambient air.

The treatments of these materials are listed in Table 3. The terminologies 1× means a single cycle of irradiation and annealing and 2× and 3× denote that the materials received the sequential cross-link process, two and three times, respectively; these materials received a nominal dose of 3.0 MRads during each step of radiation. Annealing was done at 130° C. for 8 hours after each radiation dose.

Differential Scanning Calorimetry (DSC)

DSC samples were cut from machined 1 mm thick sheets. Specimens (~4 mg) were heated from 50° C. at heating rate of 10 C./min in a Perkin-Elmer DSC 7 to 175° C. The melting temperature was determined from the peak of the melting endotherm. The heat of fusion was calculated through an integration of the area under the melting endotherm between 60° C. and 145° C. Crystallinity was calculated using the abovementioned heat of fusion divided by 288 J/g, the heat of fusion of an ideal polyethylene crystal.

Results and Discussion

The measured melting temperature and crystallinity are listed in Table 2. After the three consecutive sequential cross-link process; materials received 3.0, 6.0 and 9.0 MRads total gamma-radiation showed no change in crystallinity when comparing to material that received a 3.0 MRads gamma-radiation in a container with less than 0.5% oxygen (58% v 57.6%) while remelting caused a significant decrease in crystallinity from 57% to 48%.

TABLE 2

| Treatment | Melting Temperature, ° C. | Crystallinity, % |
|---|---|---|
| No Radiation | 135.8 ± 0.1 | 54.3 ± 0.7 |
| 3.0 MRads single dose in a Container with less than 0.5% oxygen | 139.9 ± 0.2 | 57.6 ± 0.8 |
| 1X cross-linked and annealed one time, 3.0 MRads | 140.1 ± 0.2 | 56.7 ± 0.9 |
| 2X sequentially cross-link and annealed, 6.0 MRads | 141.1 ± 0.1 | 57.4 ± 0.6 |
| 3X sequentially cross-link and annealed, 9.0 MRads | 142.3 ± 0.1 | 58.0 ± 0.9 |
| 5 MRads single dose cross-link, remelted at 150° C. for 8 hours | 137.0 ± 0.2 | 48.2 ± 0.7 |
| 10 MRads single dose cross-link, remelted at 150° C. for 8 hours | 139.7 ± 0.2 | 48.6 ± 0.6 |

Example V

Effect of Sequential Cross-Link Dose on the Tensile Properties of UHMWPE

Materials and Methods

The materials for tensile property evaluation are the same as the physical property materials described in Example IV above. Six tensile specimens were machined out of the center of the 83 mm diameter bars according to ASTM F648, Type IV and 1 mm thick. Tensile property evaluation was carried out on an electromechanical Instron model 4505 universal test frame at a speed of 50 mm/inch. The treatments of these materials are listed in Table 2.

Results and Discussion

The tensile properties (yield strength, ultimate strength and elongation at break) are illustrated in Table 3. The sequential cross-link process increased tensile yield strength following each treatment. This process also maintained ultimate tensile strength in a cross-link UHMWPE while remelt processes significantly decreased both yield and ultimate strengths when comparing to samples that received a 3.0 MRads gamma-radiation in a container with less than 0.5% oxygen.

TABLE 3

| Treatment | Yield Strength (MPa) | Ultimate Strength (MPa) | Elongation at Break (%) |
|---|---|---|---|
| No radiation | 21.4 ± 0.5 | 52.2 ± 3.1 | 380 ± 18 |
| 3.0 MRads single dose in a container with less than 0.5% oxygen | 24.5 ± 0.2 | 54.6 ± 4.0 | 356 ± 14 |
| 1X cross-link and annealed, a single time 3.0 MRads | 22.7 ± 0.2 | 50.4 ± 2.8 | 338 ± 10 |
| 2X sequentially cross-link and annealed, 6.0 MRads total dose | 23.5 ± 0.5 | 52.2 ± 3.9 | 299 ± 11 |
| 3X sequentially cross-link and annealed, 9.0 MRads total dose | 25.6 ± 0.4 | 54.8 ± 1.2 | 255 ± 7 |
| 5 MRads single dose cross-link, remelted at 150° C. for 8 hours | 21.3 ± 0.3 | 48.2 ± 3.1 | 297 ± 8 |
| 10 MRads single dose cross-link remelted at 150° C. for 8 hours | 21.6 ± 0.4 | 43.6 ± 0.7 | 260 ± 12 |

Example VI

Effect of Sequential Cross-Link Dose on the Wear Properties of UHMWPE Acetabular Cups Materials and Methods Two types of UHMWPE materials, ram extruded GUR 1050 bars (83 mm diameter) and compression molded GUR 1020 sheets (51 mm×76 mm cross-section were treated). The sequential cross-link process was performed on the GUR 1050 materials either 2 or 3 times and on GUR 1020 material 3 times only. The nominal radiation dose for each radiation/annealing cycle was 3.0 MRads. A current standard product, Trident™ design 32 mm acetabular cup (manufactured by Howmedica Osteonics Corp. from GUR 1050 bar stock) sterilized under a 3.0 MRads gamma-radiation in a container with less than 0.5% oxygen, was used as a reference material.

All acetabular cups were fabricated according to prints for the Trident™ design 32 mm insert (Howmedica Osteonics Corp. Cat. No. 620-0-32E). The standard cobalt chrome femoral heads (6260-5-132) were obtained, these femoral heads were of matching diameter to the insert inside diameter of 32 mm.

An MTS 8-station hip simulator was used to perform the wear test. The cups were inserted into metal shells as in vivo. The shells were then secured into polyethylene holders that were in turn fitted onto stainless steel spigots. Each head was mounted onto a stainless steel taper that was part of a reservoir containing a fluid serum media. The serum reservoir was mounted on a 23-degree inclined block. A standard physiological cyclic load between two peak loads of 0.64 and 2.5 kN at 1 Hz was applied to all cups. This cyclic load was applied through the central axes of the cup, head and block.

The serum used for this test was a fetal-substitute alpha calf fraction serum (ACFS) diluted to a physiologically relevant value of about 20 grams per liter of total protein. A preservative (EDTA) about 0.1 vol. % was added to minimize bacteria degradation. Each reservoir contained about 450 milliliters of abovementioned ACFS with EDTA. This fluid in the reservoir was replaced with fresh ACSS with EDTA every 250,000 cycles. During the fluid replacement process, the samples were removed from the machine, cleaned and weighed.

Results and Discussion

The wear rate of each treatment is illustrated in Table 4; the measurement unit given is cubic millimeters per million cycles (mm³/mc). The wear rate was corrected for the effect of fluid absorption. The cups subject to the 2× and 3× sequential cross-link processes significantly reduced wear rate in UHMWPE acetabular cups by 86 to 96% when comparing to cups that received a 3.0 MRads gamma-radiation in a container with less than 0.5% oxygen.

TABLE 4

| Treatment | Wear Rate (mm³/mc) | Reduction in Wear Rate (%) |
|---|---|---|
| GUR 1050 received 3.0 MRads in a container with less than 0.5% oxygen (a reference material) | 37.6 | NA |
| GUR 1050 received 2X sequentially cross-link and annealed, 6.0 MRads total | 5.3 | 86 |
| GUR 1050 received 3X sequentially cross-link and annealed, 9.0 MRads total | 1.4 | 96 |
| GUR 1020 received 3X sequentially cross-link and annealed, 9.0 MRads | 2.5 | 93 |

Example VII

Effect of Sequential Cross-Link Dose on the Free Radical Concentration in UHMWPE Materials and Methods The materials for free radical concentration evaluated were:

1. GUR 1050 that received 3.0 MRads in a container with less than 0.5% oxygen (A reference material).
2. GUR 1050 that received 2× (6.0 MRads) sequentially cross-link and annealed.
3. GUR 1050 that received 3× (9.0 MRads) sequentially cross-link and annealed.
4. GUR 1050 that received a 9.0 MRads single total dose of cross-link radiation and annealed at 130° C. for 8 hours.

The specimens are 3 mm diameter, 10 mm long cylinders fabricated from abovementioned components. This evaluation was carried out at the University of Memphis (Physics Department, Memphis, Tenn.). Free radical concentration was measured and calculated from an average of three (3) specimens. Free radical measurements were performed using electron spin resonance technique. This is the only technique that can directly detect free radicals in solid and aqueous media. A top-of-the-line ESR spectrometer (Bruker EMX) was used in this evaluation.

Results and Discussion

The free radical concentration in the materials is illustrated in Table 5; the measurement unit given is spins per grams (spins/g). The materials subjected to the 2× and 3× sequential cross-link processes showed a significant reduction in free radical concentration about 94 to 98% when comparing to a GUR 1050 material that received a 3.0 MRads gamma-radiation in a container with less than 0.5% oxygen. The materials subjected to the 2× and 3× sequential cross-link processes also showed a significant reduction in free radical concentration about 82 to 92% when comparing to a GUR 1050 material that received a 9.0 MRads total dose of gamma-radiation and annealed at 130° C. for 8 hours.

TABLE 5

| Treatment | Free Radical Concentration (10E+14 spins/g) | Reduction in Free Radical Concentration (%) |
|---|---|---|
| GUR 1050 received 3.0 MRads in a container with less than 0.5% oxygen (a reference material) | 204 ± 14 | NA |
| GUR 1050 received 2X sequentially cross-link and annealed, 6.0 MRads | 5 ± 1 | 98 |
| GUR 1050 received 3x sequentially cross-link and annealed, 9.0 MRads | 12 ± 1 | 94 |
| GUR 1050 received 9.0 MRads cross-link and annealed 130° C. for 8 hours | 67 ± 4 | 67 |

Example VIII

Effect of Sequential Cross-Link Dose on the Oxidation Resistance Property of UHMWPE Materials and Methods The materials for oxidation resistance evaluation were:

1. GUR 1050 that received 3.0 MRads in a container with less than 0.5% oxygen (A reference material).
2. GUR 1050 that received 3× (9.0 MRads) sequentially cross-link and annealed.
3. GUR 1050 that received a 9.0 MRads single total dose of cross-link radiation and annealed at 130° for 8 hours.

An accelerated aging protocol per ASTM F 2003 (5 atm oxygen pressure at 70° C. for 14 days) was carried out at Exponent Failure Analysis Associates (Philadelphia, Pa.). The specimens were machined 90×20×10 mm rectangular blocks. The oxidation analysis was performed on a Nicolet model 750 Magna-IR™ spectrometer per ASTM F2102-01 using an aperture 100 μm×100 μm and 256 scans. An oxidation index was defined by the ratio of the carbonyl peak area (1660 to 1790 cm$^{-1}$) to the 1370 cm$^{-1}$ peak area (1330 to 1390 cm$^{-1}$). A through-the-thickness (10 mm) oxidation index profile was generated from an average of three (3) specimens. The 0 and 10 mm depths represented surfaces of specimens. The maximum oxidation index of each specimen was used to determine if there was a significant difference.

Results and Discussion

Oxidation index profiles and the maximum oxidation index are illustrated in FIG. 1 and Table 6, respectively. The GUR 1050 materials subjected to the 3× sequential cross-link process showed a significant reduction in both an oxidation index profile and maximum oxidation index. The sequential cross-link process significantly reduced the maximum oxidation index in 3×GUR 1050 by 86% when comparing to a GUR 1050 material that received a 3.0 MRads gamma-radiation in a container with less than 0.5% oxygen. The GUR 1050 materials subjected to the 3× sequential cross-link process also showed a significant reduction in maximum oxidation index by 72% when comparing to a GUR 1050 material that received a 9.0 MRads total dose of gamma-radiation and annealed at 130° C. for 8 hours.

TABLE 6

| Treatment | Maximum Oxidation Index |
| --- | --- |
| GUR 1050 received 3.0 MRads in a container with less than 0.5% oxygen (a reference material) | 2.60 ± 0.02 |
| GUR 1050 received 3X sequentially cross-link and annealed, 9.0 MRads | 0.36 ± 0.02 |
| GUR 1050 received 9.0 MRads cross-link and annealed 130° C. for 8 hours | 1.29 ± 0.03 |

Example IX

Effect of Sequential Cross-Link Dose on the Wear Properties of Direct Compression Molded UHMWPE Tibial Inserts Materials and Methods All direct compression molded (DCM) and machined Howmedica Osteonics Corp. Scorpio® PS tibial inserts were fabricated from GUR 1020 UHMWPE. DCM Scorpio® PS direct molded tibial inserts were treated with the sequential cross-link process (radiation and annealing) two times (2×), a nominal dose of 4.5 MRads during each step of radiation. The total accumulation of gamma-radiation in these components was 9.0 MRads. These components were packaged in an air impermeable pouch with less than 0.5% oxygen. Scorpio® PS tibial inserts (Howmedica Osteonics Corp. Cat. No. 72-3-0708) were machined from compression molded GUR 1020 material and obtained from an in-house order. These components then received gamma-radiation sterilization at a nominal dose of 3.0 MRads in a container with less than 0.5% oxygen. Wear test was performed on an MTS knee simulator according to an ISO standard 14243 Part 3.

Results and Discussion

The wear test results are illustrated in Table 7; the measurement unit given is cubic millimeters per million cycles ($mm^3$/mc). The wear rate was corrected for the effect of fluid absorption. The DCM Scorpio® PS tibial inserts subjected to the 2× (4.5 MRad) sequential cross-link process significantly reduced wear rate in UHMWPE tibial inserts by 88% when comparing to Scorpio® PS tibial inserts that received a 3.0 MRads gamma-radiation in a container with less than 0.5% oxygen.

TABLE 7

| Treatment | Wear Rate ($mm^3$/mc) | Reduction in Wear Rate (%) |
| --- | --- | --- |
| Scorpio ® PS machined from compression molded GUR 1020, received 3.0 MRads in a container with less than 0.5% oxygen (a reference material) | 32.6 ± 6.8 | NA |
| DCM Scorpio ® PS GUR 1020 received 2X (4.5 MRads) sequentially cross-link and annealed, 9.0 MRads total | 3.8 ± 0.1 | 88 |

Example X

Effect of Sequential Cross-Link Dose on the Free Radical Concentration in Direct Compression Molded UHMWPE Tibial Inserts Materials and Methods The materials for free radical concentration evaluation are the same as the wear test materials described in Example IX, above. The specimens are 3 mm diameter, 10 mm long cylinders fabricated from abovementioned components. This evaluation was carried out at the University of Memphis (Physics Department, Memphis, Tenn.). Free radical concentration was measured and calculated from an average of three (3) specimens. Free radical measurements were performed using electron spin resonance technique. This is the only technique that can directly detect free radials in solid and aqueous media. A top-of-the-line ESR spectrometer (Bruker EMX) was used in this evaluation.

Results and Discussion

The free radical concentration in the materials is illustrated in Table 8; the measurement unit given is spins per gram (spins/g). The DCM Scorpio® PS tibial inserts subjected to the 2× (4.5 MRads) sequential cross-link processes showed a significant reduction in free radical concentration of 97% when comparing to a Scorpio® PS machined from compression molded GUR 1020 that received a 3.0 MRads of gamma-radiation sterilization in a container with less than 0.5% oxygen.

TABLE 8

| Treatment | Free Radical Concentration (10E+14 spins/g) | Reduction in Free Radical Concentration (%) |
| --- | --- | --- |
| Scorpio ® PS machined from compression molded GUR 1020, received 3.0 MRads in a container with less than 0.5% oxygen (a reference material) | 325 ± 28 | NA |
| DCM Scorpio ® PS GUR 1020 received 2X (4.5 MRads) sequentially cross-link and annealed, 9.0 MRads total | 9 ± 0 | 97 |

Example XI

Effect of Sequential Cross-Link Dose on the Oxidation Resistance of Direct Compression Molded UHMWPE Tibial Inserts Materials and Methods The materials for oxidation resistance evaluation are the same as the wear test materials described in Example IX, above. An accelerated aging protocol per ASTM F 2003 (5 atm oxygen pressure at 70° C. for 14 days) was carried out at Howmedica Osteonics (Mahwah, N.J.). The specimens were machined and sequentially cross-link 2× (4.5 MRads) DCM Scorpio® PS tibial inserts. The oxidation analysis was performed on a Nicolet model 750 Magna-IR™ spectrometer per ASTM F2102-01 using an aperture 100 μm×100 μm and 256 scans. An oxidation index was defined by the ratio of the carbonyl peak area (1660 to 1790 $cm^{-1}$) to the 1370 $cm^{-1}$ peak area (1330 to 1390 $cm^{-1}$). A through-the-thickness (about 6 mm) oxidation index profile was generated from an average of three (3) specimens. The 0 and 6 mm depths represented articulating and back surfaces of specimens. The maximum oxidation index of each specimen was used to determine if there was a significant difference.

Figure 2:
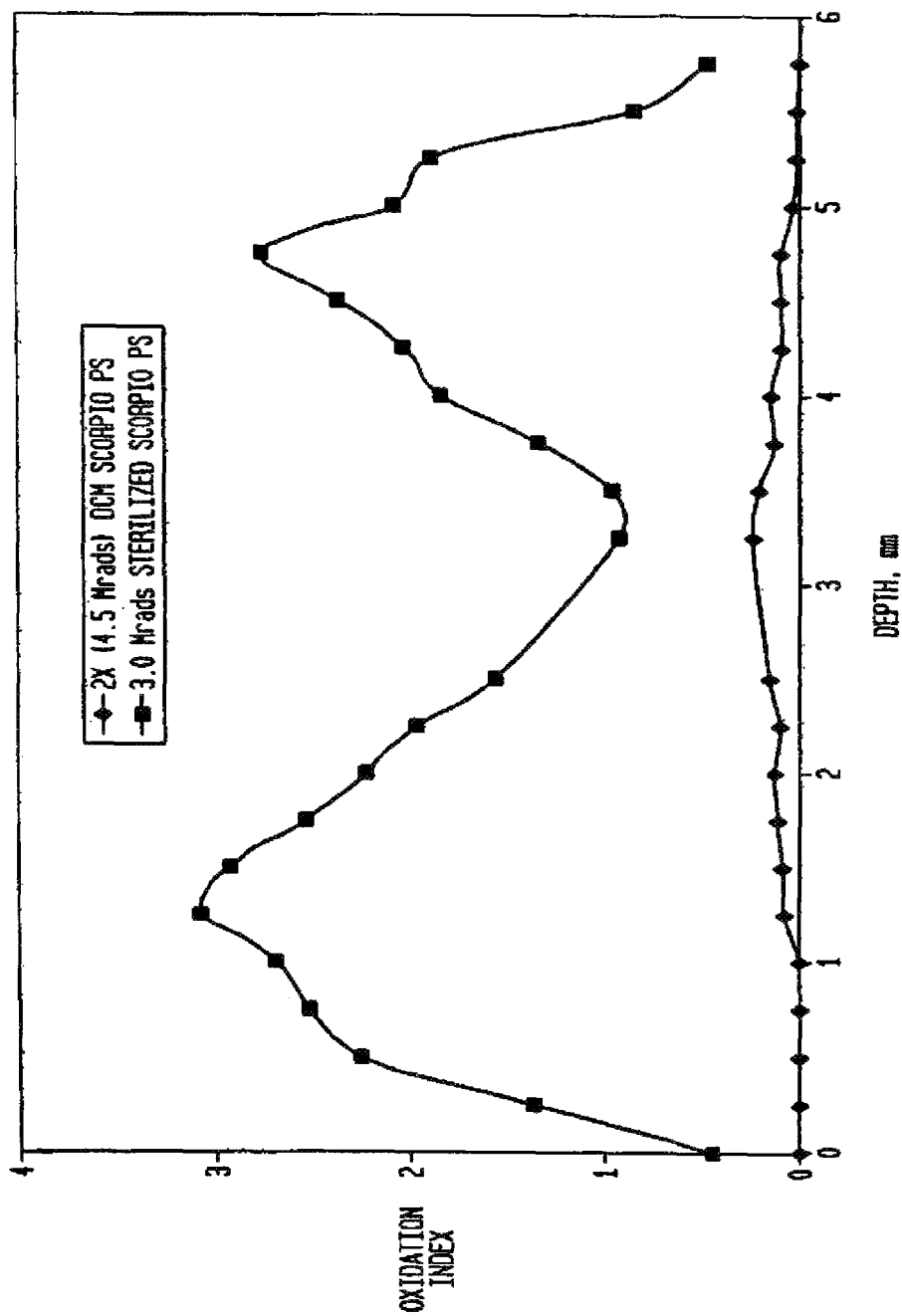
FIG. 2 shows the oxidation index profiles of the specimens of Example 11.

Results and Discussion—Oxidation index profiles and the maximum oxidation index are illustrated in FIG. 2 and Table 9, respectively. The DCM Scorpio® PS tibial inserts subjected to the 2× (4.5 MRads) sequential cross-link processes showed a significant reduction in an oxidation index profile and maximum oxidation index. The sequential cross-link process reduced the maximum oxidation index in 2× (4.5 MRads) DCM GUR 1020 Scorpio® PS tibial inserts by 90% when comparing to a Scorpio® PS machined from compression molded GUR 1020 that received a 3.0 MRads of gamma-radiation sterilization in a container with less than 0.5% oxygen (see Table 9 below).

TABLE 9

| Treatment | Maximum Oxidation Index |
| --- | --- |
| Scorpio ® PS machined from compression molded GUR 1020, received 3.0 MRads in a container with less than 0.5% oxygen (a reference material) | 3.10 ± 0.03 |
| GUR 1020 received 2X (4.5 MRads) sequentially cross-link and annealed, 9.0 MRads total | 0.30 ± 0.02 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for increasing the wear resistance of an ultra high molecular weight polyethylene (UHMWPE) medical implant comprising:
   a) heating a preformed UHMWPE in a solid state to a temperature between about 110° C. and about 135° C. but below the melting point;
   b) thereafter irradiating the preformed UHMWPE at an incremental radiation dose and maintaining the temperature for at least about 4 hours and then allowing the UHMWPE to cool;
   repeating steps a) and b) at least two more times until a total radiation dose of 5 to 10 Mrad is achieved.

2. The method for increasing the wear resistance as set forth in claim 1, wherein the total radiation dose is 9 Mrad.

3. The method for increasing the wear resistance as set forth in claim 2, wherein an incremental dose for each irradiation is 3 Mrad.

4. The method for increasing the wear resistance as set forth in claim 1, wherein the weight average molecular weight of the UHMWPE is $10^6$ to $10^7$ grams per mole prior to cross-linking with irradiation.

5. The method as set forth in claim 1 further including the step of machining the preformed UHMWPE into a medical implant.

6. The method as set forth in claim 5 wherein the irradiating and heating is performed on the preformed polyethylene prior to forming the medical implant to a final implantable shape.

7. The method as set forth in claim 1 wherein after the last irradiation and cooling the preformed UHMWPE has a free radical content of $12\pm1\times10^{14}$ spins per gram.

8. The method as set forth in claim 1 wherein after the last irradiation and heating step the preformed UHMWPE has a tensile strength of 54.8±1.2 Mpa.

9. The method as set forth in claim 1 wherein after the last irradiation and heating step the preformed UHMWPE has a crystallinity of 58±0.9%.

10. A method of making an ultrahigh molecular weight polyethylene (UHMWPE) medical implant comprising heating a preformed UHMWPE to a temperature between about 110° C. and about 135° C. but lower than the melting point, thereafter irradiating the preformed UHMWPE at least three times to a total dose of 5 to 10 Mrad maintaining the temperature for about 8 hours after each irradiation followed by cooling after each heating and thereafter forming the medical implant.

11. The method as set forth in claim 10, wherein the UHMWPE is cross-linked by a total radiation dose is about 9 Mrad.

12. The method for increasing the wear resistance as set forth in claim 11, wherein an incremental dose for each irradiation is 3 Mrad.

13. The method for increasing the wear resistance as set forth in claim 10, wherein the weight average molecular weight of the UHMWPE is $10^6$ to $10^7$ grams per mole prior to cross-linking with irradiation.

14. The method as set forth in claim 10 further including the step of machining the preformed UHMWPE into a medical implant.

15. The method as set forth in claim 10 wherein after the last irradiation and cooling the preformed UHMWPE has a free radical content of $12\pm1\times10^{14}$ spins per gram.

16. The method as set forth in claim 10 wherein after the last irradiation and heating step the preformed UHMWPE has a tensile strength of 54.8±1.2 Mpa.

17. The method as set forth in claim 10 wherein after the last irradiation and heating step the preformed UHMWPE has a crystallinity of 58±0.9%.

* * * * *